(12) United States Patent
Khayamian et al.

(10) Patent No.: US 11,187,701 B2
(45) Date of Patent: Nov. 30, 2021

(54) REAL-TIME TRACING OF CYTOKINE STORM IN BLOOD SERUM OF COVID-19 PATIENTS

(71) Applicants: Mohammad Ali Khayamian, Tehran (IR); Mohammad Abdolahad, Tehran (IR); Mohammad Salemizadeh Parizi, Tehran (IR); Mohammad Reza Ghaderinia, Tehran (IR); Hamed Abadijoo, Tehran (IR); Shohreh Vanaei, Tehran (IR); Hossein Simaee, Tehran (IR); Shahriar Shalileh, Tehran (IR); Mahsa Faramarzpour Darzini, Tehran (IR)

(72) Inventors: Mohammad Ali Khayamian, Tehran (IR); Mohammad Abdolahad, Tehran (IR); Mohammad Salemizadeh Parizi, Tehran (IR); Mohammad Reza Ghaderinia, Tehran (IR); Hamed Abadijoo, Tehran (IR); Shohreh Vanaei, Tehran (IR); Hossein Simaee, Tehran (IR); Shahriar Shalileh, Tehran (IR); Mahsa Faramarzpour Darzini, Tehran (IR)

(*) Notice: Subject to any disclaimer, the term of this patent is extended or adjusted under 35 U.S.C. 154(b) by 0 days.

(21) Appl. No.: 17/207,639

(22) Filed: Mar. 20, 2021

(65) Prior Publication Data

US 2021/0223244 A1    Jul. 22, 2021

Related U.S. Application Data

(60) Provisional application No. 63/032,734, filed on Jun. 1, 2020.

(51) Int. Cl.
*G01N 33/569* (2006.01)
*G01N 27/02* (2006.01)
*G01N 15/04* (2006.01)

(52) U.S. Cl.
CPC ..... *G01N 33/56983* (2013.01); *G01N 15/042* (2013.01); *G01N 27/026* (2013.01); *G01N 2333/165* (2013.01)

(58) Field of Classification Search
CPC .......... G01N 33/56983; G01N 27/026; G01N 15/042; G01N 2333/165
See application file for complete search history.

(56) References Cited

U.S. PATENT DOCUMENTS

2015/0369806 A1* 12/2015 Wang ..................... C23C 14/34
435/5

* cited by examiner

*Primary Examiner* — Jennifer Wecker
*Assistant Examiner* — Michael Paul Shimek
(74) *Attorney, Agent, or Firm* — Bajwa IP Law Firm; Haris Zaheer Bajwa

(57) ABSTRACT

A method for diagnosing COVID-19 infection. The method includes drawing a blood sample from a person suspected to be infected with COVID-19 virus, separating a blood serum sample from the blood sample by centrifuging the blood sample, recording an electrochemical impedance spectroscopy (EIS) associated with the blood serum sample, calculating a charge transfer resistance ($R_{CT}$) of the recorded EIS by measuring a diameter of a semicircular curved part of the recorded EIS, and detecting a COVID-19 infection of the person based on the calculated $R_{CT}$ if the calculated $R_{CT}$ is equal to or more than a threshold value.

19 Claims, 25 Drawing Sheets

ELISA

| Number of Cases: 63 | | Positive | Negative | Total |
|---|---|---|---|---|
| EIS Analysis | Positive | True Positive: 50 | False Positive: 3 | 53 |
| | Negative | False Negative: 0 | True Negative: 10 | 10 |
| | Total | 50 | 13 | |

FIG. 13A

| Number of Cases: 63 | RT-PCR | | |
|---|---|---|---|
| | Positive | Negative | Total |
| EIS Analysis Positive | True Positive: 47 | False Positive: 6 | 53 |
| Negative | False Negative: 1 | True Negative: 9 | 10 |
| Total | 48 | 15 | Sensitivity ≈ 92% Specificity ≈ 50% |

FIG. 16A

CT Scan

| Number of Cases: 63 | | Positive | Negative | Total |
|---|---|---|---|---|
| EIS Analysis | Positive | True Positive: 50 | False Positive: 3 | 53 |
| | Negative | False Negative: 1 | True Negative: 9 | 10 |
| | Total | 51 | 12 | Sensitivity ≈ 93%<br>Specificity ≈ 67% |

FIG. 16B

REAL-TIME TRACING OF CYTOKINE STORM IN BLOOD SERUM OF COVID-19 PATIENTS

CROSS-REFERENCE TO RELATED APPLICATION

This application claims the benefit of priority from pending U.S. Provisional Patent Application Ser. No. 63/032,734 filed on Jun. 1, 2020, and entitled "ELECTRICAL CYTOKINE SENSING (ECYTOSENSE) FOR COVID-19 INDIRECT SCREENING; DETECTION OF CYTOKINE STORM BY GRAPHENE ELECTRODES", which is incorporated herein by reference in its entirety.

TECHNICAL FIELD

The present disclosure generally relates to detecting cytokine storm in a patient, and particularly, to a label-free electrochemical approach to detect COVID-19 infection status of a patient by recording and analyzing an electrochemical impedance spectroscopy (EIS) of a blood serum sample of the patient.

BACKGROUND

COVID-19 as a new member of fetal coronaviruses severely infects the lower respiratory tract and leads to several common symptoms including dry cough, fever and shortness of breath in many patients. Due to the highly contagious nature of this virus due to both person-to-person and airborne transmission, along with a daily upsurge of newly infected patients globally, COVID-19 was announced as a pandemic by the World Health Organization (WHO) in 2019.

There are various aspects about COVID-19 virus which are still quite unknowns in the scientific community. However, some insight has been gleaned over the last year based on case studies. For example, after entry of COVID-19 to a respiratory tract, three phases are presumed: viral replication, immune hyperactivity or cytokine storm, and finally a pulmonary dysfunction. In fact, it appears that when infected with COVID-19, the immune system itself attacks the infected patient. When the white blood cells are faced with the virus or virus-infected cells, they become hyperactivated and unleash (secrete) a storm of cytokines into the blood medium to call other immune cells. Furthermore, reports demonstrate that cytokine storm is the most relevant reason behind the mortality of the COVID-19 patients by inducing an acute respiratory distress syndrome (ARDS). On this basis, notable fraction of clinical trials are attempting to suppress the hyperactivation of the immune system in response to diagnosis of a COVID-19 infection.

Hence, monitoring the acute elevation of cytokines could be a reliable warning approach to check the severity of the disease in the infected patients. Many methods were developed for rapid and precise tracing of cytokine storm in blood. However, many of these conventional approaches are time-consuming and have expensive protocols. Nonetheless, the conventional Enzyme-linked immunosorbent assay (ELISA) method even with its limitations such as cross-reactivity of the antibodies is still the most utilized technique among all proposed procedures.

Hence, there is still a need for a real-time, simple, cost-effective and precise method, system, and associated apparatus for fast reliable monitoring detection of cytokine storm in patients, and specifically, in patients with COVID-19 symptoms. Furthermore, there is a need for a fast-diagnosing and easy-to-use method to detect COVID-19 infection in a suspicious person to avoid further spreading the virus. Moreover, there is a need for a cost-effective and simple method to detect COVID-19 in suspected patients without any need for expensive and complicated techniques and devices.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for diagnosing COVID-19 infection. The method may include drawing a blood sample from a person suspected to be infected with COVID-19 virus, separating a blood serum sample from the blood sample by centrifuging the blood sample, recording an electrochemical impedance spectroscopy (EIS) associated with the blood serum sample, calculating a charge transfer resistance ($R_{CT}$) of the recorded EIS by measuring a diameter of a semicircular curved part of the recorded EIS, and detecting a COVID-19 infection status of the person based on the calculated $R_{CT}$ if the calculated $R_{CT}$ is equal to or more than a threshold value.

In an exemplary implementation, the method may further include generating a calibration dataset. In an exemplary implementation, generating the calibration dataset may include generating a set of $R_{CT}$ values and generating a set of total cytokine mass values corresponding to the set of $R_{CT}$ values. In an exemplary implementation, generating the set of $R_{CT}$ values may include recording a set of EIS plots from a respective plurality of blood serum samples drawn from a corresponding plurality of persons and calculating the set of $R_{CT}$ values respective to the set of recorded EIS plots by measuring a diameter of a semicircular curved part of each of the recorded EIS plots. In an exemplary implementation, generating the set of total cytokine mass values corresponding to the set of $R_{CT}$ values may include measuring total cytokines mass of each of the plurality of blood serum samples utilizing a cytokine measurement assay.

In an exemplary implementation, detecting the COVID-19 infection status of the person based on the calculated $R_{CT}$ may include comparing the calculated $R_{CT}$ with the set of $R_{CT}$ values of the calibration dataset, detecting the person is in a healthy (normal) state if the calculated $R_{CT}$ is within a first range of the calibration dataset, detecting the person is in a moderately COVID-19 infected state if the calculated $R_{CT}$ is within a second range of the calibration dataset, and detecting the person is in a severely infected state if the calculated $R_{CT}$ is within a third range of the calibration dataset. In an exemplary embodiment, the first range of the calibration dataset may include a first set of $R_{CT}$ values less than the threshold value. The first set of $R_{CT}$ values may be measured from a group of healthy people. In an exemplary embodiment, the second range of the calibration dataset may include a second set of $R_{CT}$ values between the threshold value and a severity borderline value. The second set of $R_{CT}$ values may be measured from a group of moderately infected patients with COVID-19 who may have moderate levels of cytokines. In an exemplary embodiment, the third range of the calibration dataset may include a third set of $R_{CT}$ values more than the severity borderline value. The third set of $R_{CT}$ values may be measured from a group of severely infected patients with COVID-19 who may have high levels of cytokines.

In an exemplary implementation, detecting the COVID-19 infection status of the person may include detecting the Covid-19 infection of the person if the calculated $R_{CT}$ is equal to or more than 440Ω. In an exemplary implementation, detecting the COVID-19 infection status of the person may include detecting a healthy (normal) state for the person if the calculated $R_{CT}$ is less than 340Ω, detecting a moderate COVID-19 infection of the person if the calculated RCT is between 440Ω and 610Ω, and detecting a severe COVID-19 infection of the person if the calculated RCT is more than 715Ω.

In an exemplary implementation, recording the EIS associated with the blood serum sample may include forming a mixture by mixing the blood serum sample with an electrolyte solution comprising a solution of at least one metal ion, putting the mixture in contact with three-integrated electrodes of a biosensor, and recording the EIS of the mixture in contact with the three-integrated electrodes using an electrochemical stimulator-analyzer.

In an exemplary implementation, recording the EIS from the mixture in contact with the three-integrated electrodes may include recording the EIS of the mixture in contact with the three-integrated electrodes at an AC potential amplitude between 5 mV and 20 mV while sweeping a frequency range between 0.01 Hz and 100 kHz. In an exemplary embodiment, the electrochemical stimulator-analyzer may include a potentiostat.

In an exemplary implementation, putting the mixture in contact with the three-integrated electrodes of the biosensor may include dropping the mixture on a surface of three-integrated electrodes of the biosensor. In an exemplary embodiment, the three-integrated electrodes may include a working electrode including a circular-shaped sensing part, a counter electrode including a partially annular part placed around the circular-shaped sensing part of the working electrode, and a reference electrode placed adjacent to both the circular-shaped sensing part of the working electrode and the partially annular part of the counter electrode.

In an exemplary embodiment, the circular-shaped sensing part of the working electrode may include a bilayer of graphene/copper adhered on a first bilayer of gold/titanium (Au/Ti) deposited on a substrate. The working electrode may be configured to be an attachment site for the mixture. In an exemplary embodiment, the counter electrode may include a second bilayer of Au/Ti deposited on the substrate. The counter electrode may be configured to acquire an electrical response from the working electrode. In an exemplary embodiment, the reference electrode may include a third bilayer of Au/Ti deposited on the substrate. The reference electrode may be configured to adjust a specific voltage between the working and the counter electrodes.

In an exemplary embodiment, the bilayer of graphene/copper may include a layer of graphene sheets with a thickness between 0.1 nm and 1 nm deposited on a layer of copper with a thickness between 1 μm and 30 μm. In an exemplary embodiment, each of the bilayers of Au/Ti may include a layer of gold with a thickness between 10 nm and 50 nm deposited on a layer of titanium with a thickness between 3 nm and 10 nm. In an exemplary embodiment, the substrate may include at least one of a glass substrate, a silicon substrate, a ceramic substrate, and combinations thereof.

In another aspect of the present disclosure, an exemplary method for measuring a level of total cytokines in a blood serum sample is disclosed. The method may include recording an electrochemical impedance spectroscopy (EIS) associated with the blood serum sample, calculating a charge transfer resistance ($R_{CT}$) of the recorded EIS by measuring a diameter of a semicircular curved part of the recorded EIS, and determining the level of total cytokines in the blood serum sample based on the calculated $R_{CT}$ by looking up the calculated $R_{CT}$ in a calibration dataset comprising a set of total cytokine mass values respective to a set of $R_{CT}$ values.

In an exemplary implementation, the method may further include generating the calibration dataset. In an exemplary implementation, generating the calibration dataset may include generating the set of $R_{CT}$ values and generating the set of total cytokine mass values corresponding to the set of $R_{CT}$ values. In an exemplary implementation, generating the set of $R_{CT}$ values may include recording a set of EIS plots from a respective plurality of blood serum samples drawn from a corresponding plurality of persons and calculating the set of $R_{CT}$ values respective to the set of recorded EIS plots by measuring a diameter of a semicircular curved part of each of the recorded EIS plots. In an exemplary implementation, generating the set of total cytokine mass values corresponding to the set of $R_{CT}$ values may include measuring total cytokines mass of each of the plurality of blood serum samples utilizing a cytokine measurement assay.

In an exemplary implementation, determining the level of total cytokines in the blood serum sample based on the calculated $R_{CT}$ further may include diagnosing an infection of a chronic inflammatory disease (CID). In an exemplary implementation, diagnosing the CID may include detecting the infection of a chronic inflammatory disease for a person associated with the blood serum sample if the calculated $R_{CT}$ is more than a threshold value.

In an exemplary implementation, determining the level of total cytokines in a blood serum sample based on the calculated $R_{CT}$ may further include grading a severity of the chronic inflammatory disease infection of the person. In an exemplary implementation, grading the severity of the chronic inflammatory disease infection of the person may include detecting the person is in a healthy (normal) state if the calculated $R_{CT}$ is within a first range of the calibration dataset, detecting the person is in a moderately infected state if the calculated $R_{CT}$ is within a second range of the calibration dataset, and detecting the person is in a severely infected state if the calculated $R_{CT}$ is within a third range of the calibration dataset. Where, the first range of the calibration dataset may include a first set of $R_{CT}$ values less than the threshold value measured from a group of healthy people. The second range of the calibration dataset may include a second set of $R_{CT}$ values between the threshold value and a severity borderline value measured from a group of patients with moderate levels of cytokines. The third range of the calibration dataset may include a third set of $R_{CT}$ values more than the severity borderline value measured from a group of patients with high levels of cytokines.

In an exemplary implementation, recording the EIS associated with the blood serum sample may include drawing a blood sample from a person, separating the blood serum sample from the blood sample by centrifuging the blood sample, forming a mixture by mixing the blood serum sample with an electrolyte solution comprising at least one metal ion, putting the mixture in contact with three-integrated electrodes of a biosensor, and recording an EIS from the mixture in contact with the three-integrated electrodes using an electrochemical stimulator-analyzer.

In an exemplary implementation, recording the EIS from the mixture in contact with the three-integrated electrodes may include recording the EIS of the blood serum sample in contact with the three-integrated electrodes at an AC potential amplitude between 5 mV and 20 mV while sweeping a frequency range between 0.01 Hz and 100 kHz.

In an exemplary implementation, putting the mixture in contact with the three-integrated electrodes of the biosensor may include dropping the mixture on a surface of three-integrated electrodes of the biosensor. In an exemplary embodiment, the three-integrated electrodes may include a working electrode including a circular-shaped sensing part, a counter electrode including a partially annular part placed around the circular-shaped sensing part of the working electrode, and a reference electrode placed adjacent to both the circular-shaped sensing part of the working electrode and the partially annular part of the counter electrode.

In an exemplary embodiment, the circular-shaped sensing part of the working electrode may include a bilayer of graphene/copper adhered on a first bilayer of gold/titanium (Au/Ti) deposited on a substrate. The working electrode may be configured to be an attachment site for the mixture. In an exemplary embodiment, the counter electrode may include a second bilayer of Au/Ti deposited on the substrate. The counter electrode may be configured to acquire the electrical response from the working electrode. In an exemplary embodiment, the reference electrode may include a third bilayer of Au/Ti deposited on the substrate. The reference electrode may be configured to adjust a specific voltage between the working and the counter electrodes.

In an exemplary embodiment, the bilayer of graphene/copper may include a layer of graphene sheets with a thickness between 0.1 nm and 1 nm deposited on a layer of copper with a thickness between 1 μm and 30 μm. In an exemplary embodiment, each of the bilayers of Au/Ti may include a layer of gold with a thickness between 10 nm and 50 nm deposited on a layer of titanium with a thickness between 3 nm and 10 nm. In an exemplary embodiment, the substrate may include at least one of a glass substrate, a silicon substrate, a ceramic substrate, and combinations thereof.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 13A shows confusion matrix of diagnostic results obtained by EIS analysis and ELISA method for 63 persons, consistent with one or more exemplary embodiments of the present disclosure.

FIG. 16A shows confusion matrix of diagnostic results obtained by EIS analysis and RT-PCR method for 63 persons, consistent with one or more exemplary embodiments of the present disclosure.

FIG. 16B shows confusion matrix of diagnostic results obtained by EIS analysis and CT scan method for 63 persons, consistent with one or more exemplary embodiments of the present disclosure.

DETAILED DESCRIPTION

Figure 1A:
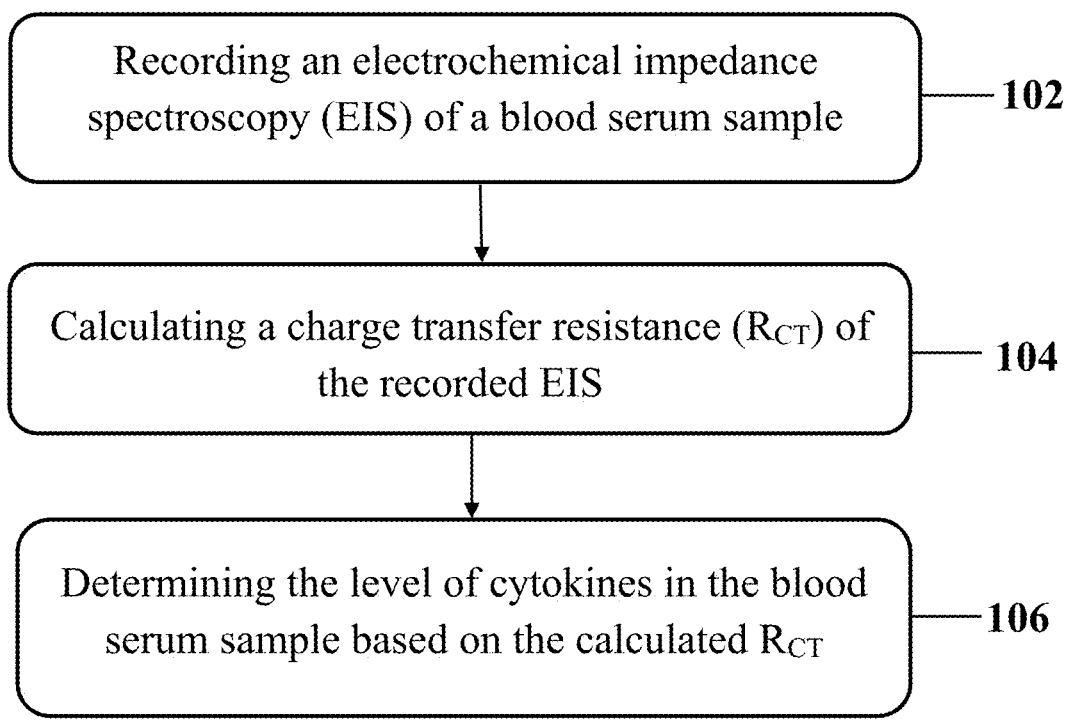
FIG. 1A shows an exemplary method for measuring a level of cytokines in a blood serum sample, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Blood serum consists of many proteins including antibodies, cytokines, hormones, etc. with different molecular weights and dielectric properties. In chronic inflammatory diseases with pathogens such as SARS-CoV-2 virus, many inflammatory signals are produced and cytokine release into the blood serum becomes out of control. Such a phenomenon is so-called cytokine storm and is the most prominent feature of the disease.

Concurrent with the pandemic announcement of SARS-CoV-2 infection by World Health Organization (WHO), a variety of reports were published affirming the cytokine storm having the most significant impact on mortality of infected patients with COVID-19 virus. Although cytokine storm arises in many other types of diseases such as sepsis, Flu, Graft versus host disease (GvHD), etc., currently the best available cohort with significant level of cytokine storm for developing new technologies is COVID-19 infected patients during this pandemic. Hence, cytokine storm as an evidenced consequence in most of the COVID-19 patients could offer a promising opportunity to use blood as a disease progression marker of COVID-19 infection.

Herein, a label-free electrochemical impedimetric approach for monitoring a level of cytokines and detecting cytokine storm in an unprocessed blood sample is disclosed. In an exemplary implementation, the disclosed method may be utilized for real-time monitoring amounts of cytokines in a person's bloodstream, and subsequently diagnosing a cytokine storm as a reliable indicator of an inflammatory disease, such as COVID-19 infection. Herein, an electrochemical impedimetric biosensor, a system including the electrochemical impedimetric biosensor, and a method utilizing the electrochemical impedimetric biosensor and the system is disclosed for simply, real-time and accurately detecting cytokines level in a blood sample, and thereafter detecting an inflammatory disease infectious in the blood sample.

Exemplary biosensor, system and method disclosed here, utilizes electrochemical impedance spectroscopy (EIS) by measuring electrical impedance of cytokines of a blood sample in an electrolyte medium. Charge transfer resistance ($R_{CT}$) is a comparing parameter between studied groups and a reliable criterion, which may be affected by a presence of dielectric materials in a media. Hence, impact of a glycoprotein cytokine on $R_{CT}$ elevation due to its weight may be expected especially for a blood serum drawn from a COVID-19 patient with a cytokine storm indication.

EIS may be utilized for quantifying overall immune activity of patients. Herein, a biosensing method for non-direct detection of cytokine storm in an inflammatory disease infected patients (e.g., COVID-19 infected patients) and their screening according to a severity of their immune activity based on a recorded EIS of cytokine storm in an unprocessed blood serum sample is disclosed. To improve electrochemical interface between biological macromolecules (such as cytokines) and electrodes, nanomaterials may be the best choice for an active surface of an electrode (e.g., a working electrode) of an electrochemical impedimetric biosensor. Herein, graphene sheets deposited on copper substrate due to its better charge mobility and electrical conductivity may be utilized as a working electrode of an electrochemical impedimetric biosensor. Moreover, graphene may apply much better site binding with polarizable bio-agents, such as cytokines in comparison with other possible usable materials, such as gold and carbon for coating on an exemplary working electrode. In an exemplary embodiment, a blood serum sample may have more tendency to a graphene layer on an electrode in comparison with a layer of gold or carbon. Exemplary biosensor, system and method may show a meaningful correlation between an immune hyperactivation in COVID-19 patients (induced by acute elevation of total mass of cytokines in blood serum) and an increased $R_{CT}$. In addition, EIS results obtained by exemplary method may be compared and approved with a cytokine mass measurement technique, such as enzyme-linked immunosorbent assay (ELISA) analysis. Moreover, exemplary biosensor may be utilized for indirect detection of patients suffering from the COVID-19 disease and results may be validated by conventional Reverse transcription polymerase chain reaction (RT-PCR) and computed tomography (CT) scan techniques on normal and infected cases.

FIG. 1A shows exemplary method 100 for measuring a level of cytokines in a blood serum sample, consistent with one or more exemplary embodiments of the present disclosure. Exemplary method 100 may include recording an electrochemical impedance spectroscopy (EIS) associated with the blood serum sample (step 102), calculating a charge transfer resistance ($R_{CT}$) of the recorded EIS by measuring a diameter of a semicircular curved part of the recorded EIS (step 104), and determining the level of cytokines in the blood serum sample based on the calculated $R_{CT}$ by looking up the calculated $R_{CT}$ in a calibration dataset comprising a set of cytokine mass values versus a set of $R_{CT}$ values (step 106).

Figure 2:
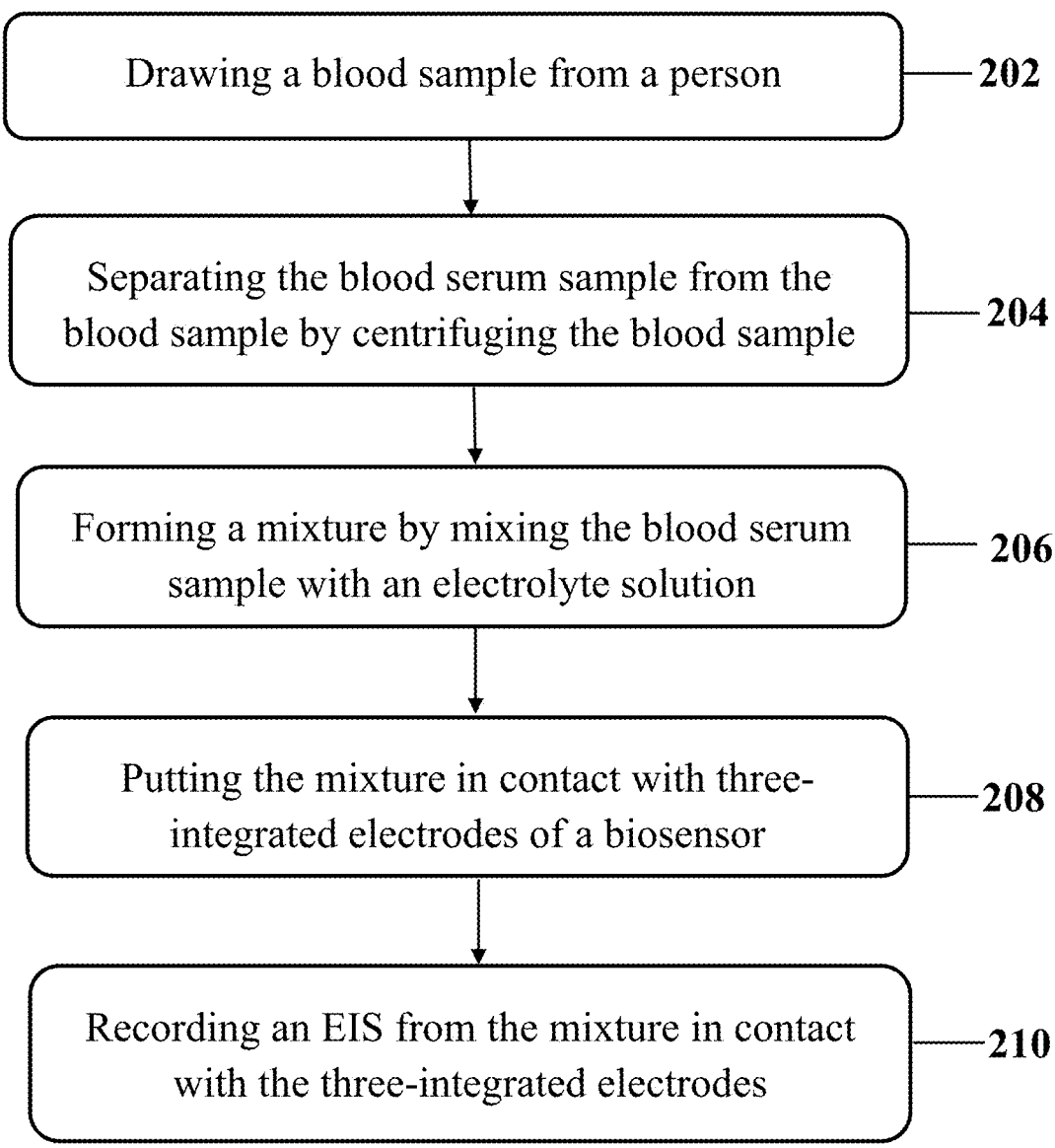
FIG. 2 shows an exemplary method for recording the electrochemical impedance spectroscopy (EIS) associated with the blood serum sample, consistent with one or more exemplary embodiments of the present disclosure.

In detail, step 102 may include recording an electrochemical impedance spectroscopy (EIS) associated with the blood serum sample. In an exemplary implementation, recording the EIS associated with the blood serum sample may include recording an EIS of the blood serum sample. FIG. 2 shows an exemplary method 200 for recording the EIS associated with the blood serum sample (step 102), consistent with one or more exemplary embodiments of the present disclosure. In an exemplary implementation, recording the EIS associated with the blood serum sample (step 102) may include drawing a blood sample from a person (step 202), separating the blood serum sample from the blood sample by centrifuging the blood sample (step 204), forming a mixture by mixing the blood serum sample with an electrolyte solution (step 206), putting the mixture in contact with three-integrated electrodes of a biosensor (step 208), and recording an EIS from the mixture in contact with the three-integrated electrodes using an electrochemical stimulator-analyzer (step 210).

In detail, step 202 may include drawing a blood sample from a person. In an exemplary embodiment, exemplary method 100 may be utilized for measuring a level of cytokines in a blood serum sample extracted from a blood sample drawn from a person suspected to be infected with COVID-19 virus. In an exemplary implementation, drawing the blood sample from the person (step 202) may include drawing a blood sample from a person suspected to be infected with COVID-19 virus. In an exemplary implementation, drawing the blood sample from the person may include drawing a blood sample between about 200 μL and about 1 cc blood sample from the person.

In an exemplary implementation, separating the blood serum sample from the blood sample (step 204) may include forming the blood serum sample in a separated phase from the blood sample by centrifuging the blood sample and extracting the blood serum sample from a top part of the centrifuged blood sample. In an exemplary implementation, centrifuging the blood sample may include centrifuging the blood sample at a speed of about 3000 rpm for about 10 minutes.

In an exemplary implementation, forming a mixture by mixing the blood serum sample with an electrolyte solution (step 206) may include mixing the blood serum sample with a solution containing one or more metal ions. The one or more metal ions may be used as a charge carrier agent for EIS measurements and recordings. In an exemplary embodiment, the solution containing one or more metal ions may include a solution of potassium ferricyanide ($K_3Fe(CN)_6$ and/or $K_4Fe(CN)_6$) with a concentration of about 5 mM of the potassium ferricyanide in water.

Figure 3A:
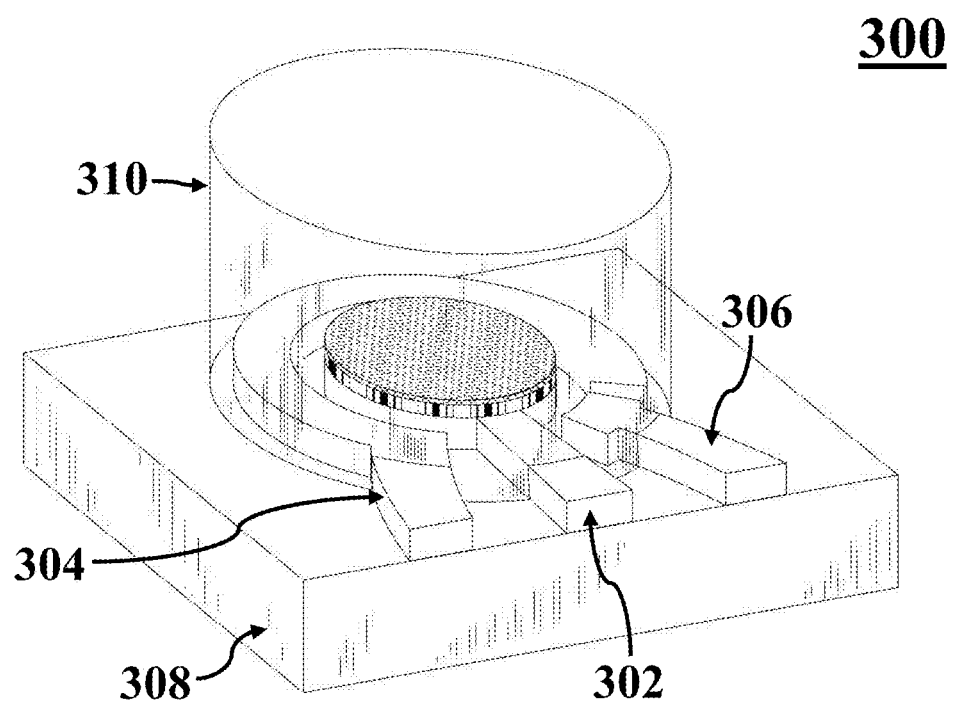
FIG. 3A shows a schematic view of an exemplary biosensor for recording an EIS from a blood serum sample, consistent with one or more exemplary embodiments of the present disclosure.

In an exemplary implementation, putting the mixture in contact with three-integrated electrodes of a biosensor (step 208) may include dropping the mixture on a surface of the three-integrated electrodes of the biosensor. FIG. 3A shows a schematic view of an exemplary biosensor 300 for recording an EIS from a blood serum sample, consistent with one or more exemplary embodiments of the present disclosure. In an exemplary embodiment, biosensor 300 may include three-integrated electrodes 302, 304, and 306 patterned and fabricated on exemplary substrate 308.

In an exemplary embodiment, substrate 308 may include at least one of a glass substrate, a silicon substrate, a ceramic substrate, and combinations thereof. In an exemplary embodiment, substrate 308 may have a thickness between about 0.5 mm and about 5 mm.

Figure 3B:
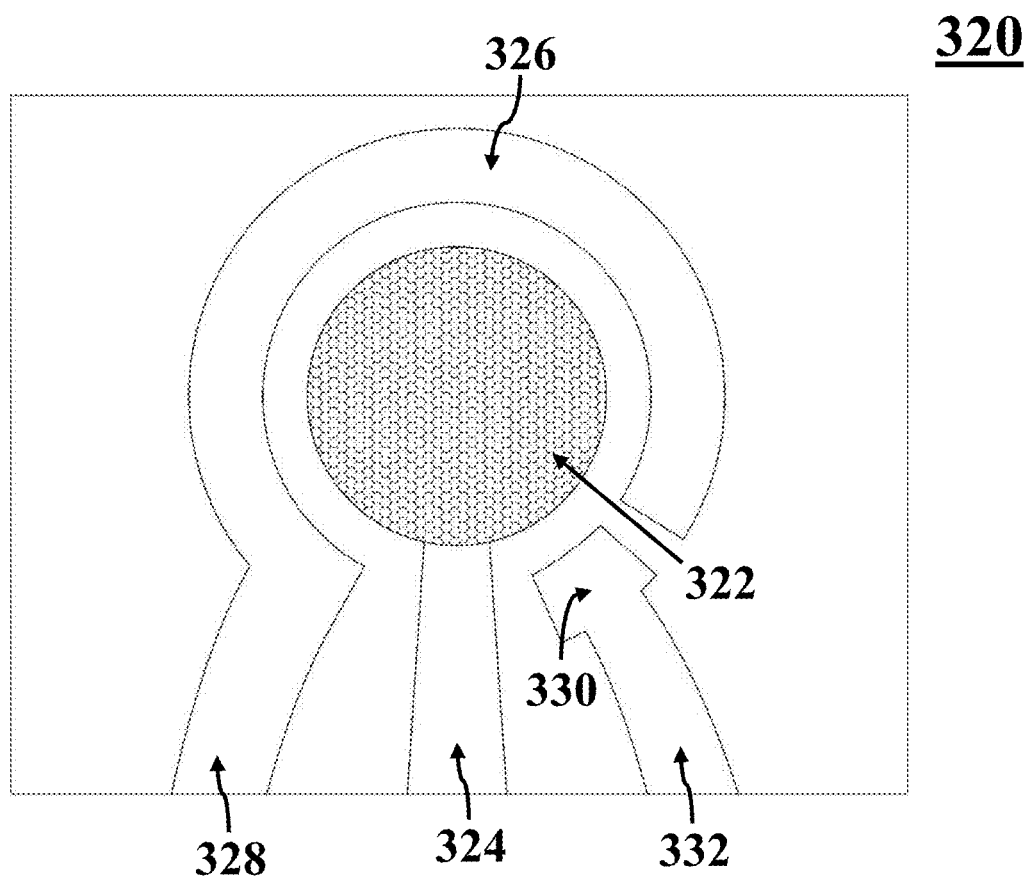
FIG. 3B shows a schematic view of an exemplary upper surface of an exemplary biosensor for recording an EIS from a blood serum sample, consistent with one or more exemplary embodiments of the present disclosure.

In an exemplary embodiment, three-integrated electrodes 302, 304, and 306 may include working electrode 302, counter electrode 304, and reference electrode 306. FIG. 3B shows a schematic view of upper surface 320 of biosensor 300 shown in FIG. 3A, consistent with one or more exemplary embodiments of the present disclosure.

Referring to FIG. 3B, working electrode 302 may include exemplary circular-shaped sensing part 322 and a first distal end 324. In an exemplary embodiment, circular-shaped sensing part 322 of working electrode 302 may be configured to be an attachment site for a sample, such as the mixture of the blood serum sample and the electrolyte solution. In an exemplary embodiment, the first distal end 324 may be configured to be connected to an electrochemical stimulator-analyzer, for example, a potentiostat device.

In an exemplary embodiment, working electrode 302 may include a first bilayer of gold/titanium (Au/Ti) deposited on upper surface 320 of biosensor 300. In an exemplary embodiment, the first bilayer of Au/Ti may include a layer of Ti with a thickness between about 3 nm and about 10 nm deposited on upper surface 320 of biosensor 300 and a layer of Au with a thickness between about 10 nm and about 50 nm deposited on the layer of Ti. Accordingly, the first distal end 324 may include the first bilayer of Au/Ti deposited on upper surface 320 of biosensor 300. In an exemplary embodiment, circular-shaped sensing part 322 may further include a layer of an electrical conductive hydrophilic material adhered on the first bilayer of Au/Ti deposited on upper surface 320 of biosensor 300. In an exemplary embodiment, circular-shaped sensing part 322 may include a bilayer of graphene/copper adhered on the first bilayer of Au/Ti. In an exemplary embodiment, the bilayer of graphene/copper may include a monolayer of graphene including a layer of graphene sheets with a thickness between about 0.1 nm and about 1 nm deposited on a layer of copper (Cu) with a thickness between about 1 μm and about 30 μm. In an exemplary embodiment, the first bilayer of Au/Ti may be deposited on upper surface 320 of biosensor 300 utilizing a sputtering technique.

Referring again to FIG. 3B, counter electrode 304 may include partially annular part 326 and a second distal end 328. In an exemplary embodiment, partially annular part 326 of counter electrode 304 may be placed around circular-shaped sensing part 322 of working electrode 302. In an exemplary embodiment, partially annular part 326 of counter electrode 304 may be configured to acquire an electrical response from working electrode 302. In an exemplary embodiment, the second distal end 328 may be configured to be connected to the electrochemical stimulator-analyzer, for example, a potentiostat device.

In an exemplary embodiment, counter electrode 304 may include a second bilayer of Au/Ti deposited on upper surface 320 of biosensor 300. In an exemplary embodiment, the second bilayer of Au/Ti may include a layer of Ti with a thickness between about 3 nm and about 10 nm deposited on upper surface 320 of biosensor 300 and a layer of Au with a thickness between about 10 nm and about 50 nm deposited on the layer of Ti. In an exemplary embodiment, the second bilayer of Au/Ti may be deposited on upper surface 320 of biosensor 300 utilizing the sputtering technique.

With more reference to FIG. 3B, reference electrode 306 may include active part 330 and a third distal end 332. In an exemplary embodiment, active part 330 of reference electrode 306 may be placed adjacent to both working electrode 302 and counter electrode 304. In an exemplary embodiment, active part 330 of reference electrode 306 may be configured to adjust a specific voltage between working electrode 302 and counter electrode 304. In an exemplary embodiment, the third distal end 332 may be configured to be connected to the electrochemical stimulator-analyzer, for example, a potentiostat device.

In an exemplary embodiment, reference electrode 306 may include a third bilayer of Au/Ti deposited on upper surface 320 of biosensor 300. In an exemplary embodiment, the third bilayer of Au/Ti may include a layer of Ti with a thickness between about 3 nm and about 10 nm deposited on upper surface 320 of biosensor 300 and a layer of Au with a thickness between about 10 nm and about 50 nm deposited on the layer of Ti. In an exemplary embodiment, the third bilayer of Au/Ti may be deposited on upper surface 320 of biosensor 300 utilizing the sputtering technique.

In further detail with respect to FIG. 3A, in an exemplary embodiment, biosensor 300 may further include exemplary liquid holder 310. In an exemplary embodiment, liquid holder 310 may be configured to hold a sample, such as the mixture of the blood serum sample and the electrolyte solution there inside on surface of three-integrated electrodes 302, 304, and 306. In an exemplary embodiment, liquid holder 310 may be placed around circular-shaped sensing part 322 of working electrode 302, partially annular part 326 of counter electrode 304, and active part 330 of reference electrode 306.

Referring back to FIG. 2, step 210 may include recording an EIS from the mixture in contact with three-integrated electrodes 302, 304, and 306 using an electrochemical stimulator-analyzer. In an exemplary implementation, recording the EIS from the mixture in contact with three-integrated electrodes 302, 304, and 306 may include recording the EIS of the mixture in contact with three-integrated electrodes 302, 304, and 306 at a AC potential amplitude between about 5 mV and 2 about 0 mV while sweeping a frequency range between about 0.01 Hz and about 100 kHz. In an exemplary embodiment, the electrochemical stimulator-analyzer may include a potentiostat device.

Figure 4:
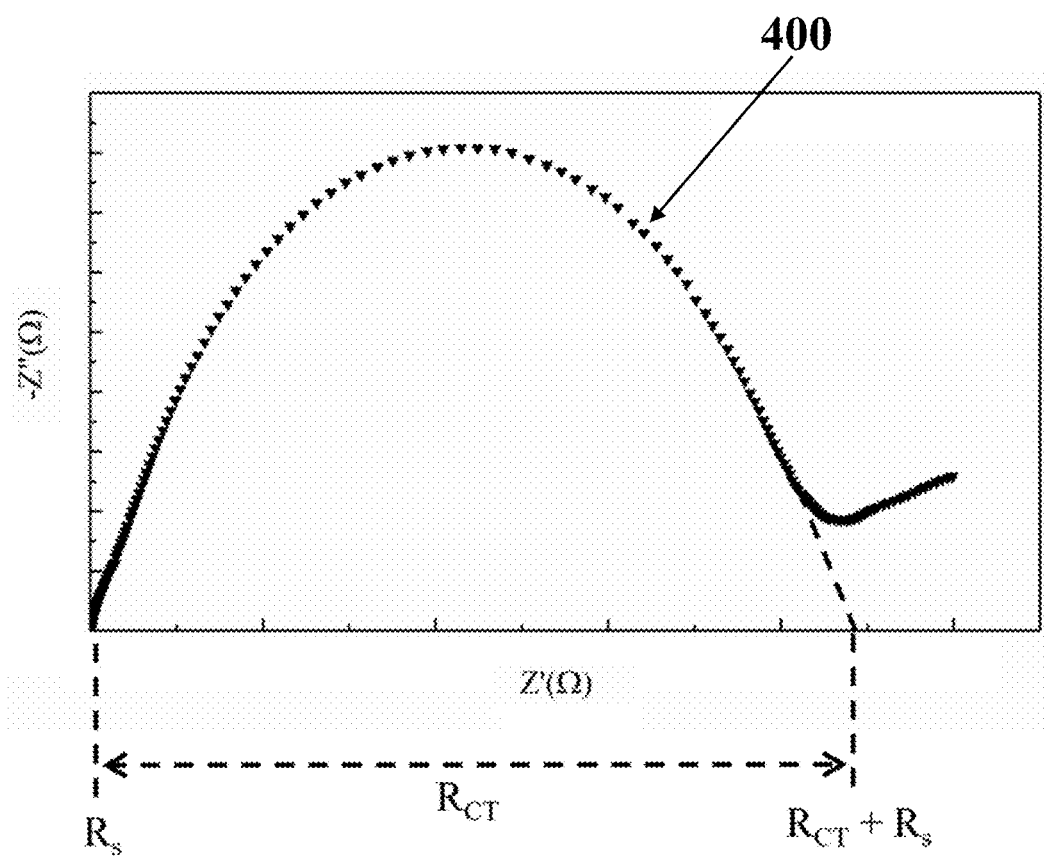
FIG. 4 shows a schematic view of an exemplary EIS response recorded from a mixture of a blood serum sample and an electrolyte solution put in contact with exemplary three-integrated electrodes, consistent with one or more exemplary embodiments of the present disclosure.

In an exemplary implementation, recording the EIS from the mixture in contact with three-integrated electrodes 302, 304, and 306 (step 210) may include plotting a Nyquist response for the blood serum sample. FIG. 4 shows a schematic view of exemplary EIS response 400 recorded from a mixture of a blood serum sample and an electrolyte solution put in contact with three-integrated electrodes 302, 304, and 306, consistent with one or more exemplary embodiments of the present disclosure. Exemplary EIS response 400 may include exemplary Nyquist plot 400 with a semicircular curve shape including a set of recorded imaginary part of impedance (Z"(Ω)) versus a set of recorded real part of impedance (Z'(Ω)).

Referring back to FIG. 1A, step 104 may include calculating a charge transfer resistance ($R_{CT}$) of the recorded EIS by measuring a diameter of a semicircular curved part of the recorded EIS obtained from step 102. In an exemplary implementation, calculating the $R_{CT}$ of the recorded EIS may include measuring a diameter of a semicircular curve of exemplary EIS 400 as shown in FIG. 4.

Moreover, step 106 of exemplary method 100 may include determining the level of total cytokines in the blood serum sample based on the calculated $R_{CT}$. In an exemplary implementation, determining the level of total cytokines in the blood serum sample based on the calculated $R_{CT}$ may include looking up the calculated $R_{CT}$ in a calibration dataset comprising a set of total cytokine mass values respective to a set of $R_{CT}$ values.

Figure 1B:
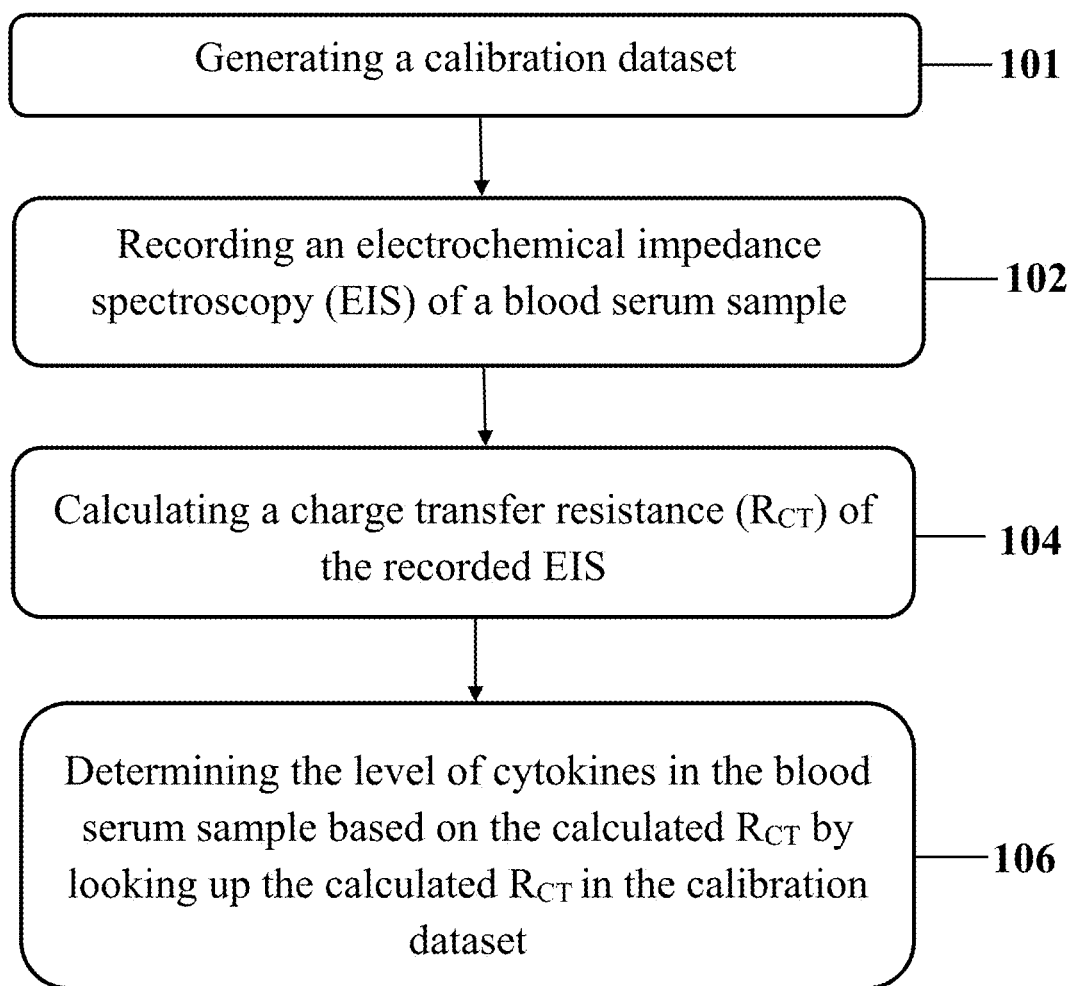
FIG. 1B shows another exemplary implementation of an exemplary method for measuring a level of cytokines in a blood serum sample, consistent with one or more exemplary embodiments of the present disclosure.

In an exemplary implementation, exemplary method 100 may further include generating the calibration dataset. FIG. 1B shows another exemplary implementation of exemplary method 110 for measuring a level of cytokines in a blood serum sample, consistent with one or more exemplary embodiments of the present disclosure. Exemplary method 110 may include generating a calibration dataset including a set of total cytokines mass values respective to a set of $R_{CT}$ values (step 101), recording an electrochemical impedance spectroscopy (EIS) associated with the blood serum sample (step 102), calculating a charge transfer resistance ($R_{CT}$) of the recorded EIS by measuring a diameter of a semicircular curved part of the recorded EIS (step 104), and determining the level of cytokines in the blood serum sample based on the calculated $R_{CT}$ by looking up the calculated $R_{CT}$ in the calibration dataset (step 106).

In detail, step 101 may include generating a calibration dataset including a set of total cytokines mass values respective to a set of $R_{CT}$ values. In an exemplary implementation, generating the calibration dataset (step 101) may include generating the set of $R_{CT}$ values and generating the set of total cytokines mass values corresponding to the set of $R_{CT}$ values.

In an exemplary implementation, generating the set of $R_{CT}$ values may include recording a set of electrochemical impedance spectroscopy (EIS) plots from a respective plurality of blood serum samples drawn from a corresponding plurality of persons and calculating the set of $R_{CT}$ values respective to the set of recorded EIS plots by measuring a diameter of a semicircular curved part of each of the recorded EIS plots. In an exemplary implementation, recording the set of EIS plots from the respective plurality of blood serum samples may be carried out similar to step 102 of exemplary method 100 described in detail hereinabove. In an exemplary implementation, calculating the set of $R_{CT}$ values respective to the set of recorded EIS plots may be carried out similar to step 104 of exemplary method 100 described in detail hereinabove.

In an exemplary implementation, generating the set of total cytokines mass values corresponding to the set of $R_{CT}$ values may include measuring total cytokines mass of each of the plurality of blood serum samples utilizing a cytokine measurement assay. In an exemplary embodiment, the cytokine measurement assay may include at least one of enzyme-linked immunosorbent assay (ELISA), Matrix-assisted laser desorption/ionization mass spectrometry (MALDI MS), and combinations thereof.

In an exemplary implementation, determining the level of total cytokines in the blood serum sample based on the calculated $R_{CT}$ (step 106) may include looking up the calculated $R_{CT}$ in the calibration dataset by comparing the calculated $R_{CT}$ with $R_{CT}$ values in the calibration dataset and obtaining a respective total cytokines mass value corresponding to the calculated $R_{CT}$ in the calibration dataset.

In an exemplary implementation, determining the level of total cytokines in the blood serum sample based on the calculated $R_{CT}$ (step 106) may further include diagnosing an infection of a chronic inflammatory disease (CID) such as COVID-19 infection. In an exemplary implementation, diagnosing the infection of the chronic inflammatory disease may include diagnosing the infection of the chronic inflammatory disease in a person associated with the blood serum sample whom the blood sample may be drawn from her. In an exemplary implementation, diagnosing the infection of the chronic inflammatory disease in the person associated with the blood serum sample may include detecting the infection of the chronic inflammatory disease for the person responsive to the calculated $R_{CT}$ being more than a threshold value. In an exemplary embodiment, the chronic inflammatory disease (CID) may include at least one of COVID-19 disease, SARS-CoV-2 infection, flu, Graft versus host disease (GvHD), and combinations thereof. In an exemplary embodiment, the threshold value may include a $R_{CT}$ value of about 340Ω for COVID-19 infection. In an exemplary embodiment, the threshold value may include a $R_{CT}$ value of about 440Ω for COVID-19 infection.

In an exemplary implementation, generating the calibration dataset (step 101) may include generating a calibration dataset from a plurality of persons including three groups of persons based on a grade of infection of the chronic inflammatory disease. The plurality of persons may be categorized in three groups, including a first group including healthy (normal) persons, a second group including moderately infected persons, and a third group including severely infected persons. The healthy (normal) persons may include a plurality of persons with no symptoms and no clinical diagnosis of an infection of the chronic inflammatory disease. The healthy (normal) persons may include a plurality of persons with total cytokines mass values of their blood serum samples less than a reference value. The second group may include a plurality of moderately infected persons with the chronic inflammatory disease that may be diagnosed and categorized by clinical diagnosis methods and assays. The third group may include a plurality of severely infected persons with the chronic inflammatory disease that may be diagnosed and categorized by clinical diagnosis methods and assays.

In an exemplary implementation, people may be categorized in three groups of persons including the first group including healthy (normal) persons, the second group including moderately infected persons, and the third group including severely infected persons based on clinical judgments and assays. The three groups of persons may be addressed with known status of severity of the chronic inflammatory disease based on clinical results and judgments. In an exemplary implementation, a plurality of persons may be clinically classified into a first group of healthy persons, a second group of moderately COVID-19 infected patients, and a third group of severely COVID-19 infected patients. The calibration dataset may be generated in step 101 for the first group of healthy persons, the second group of moderately COVID-19 infected patients, and the third group of severely COVID-19 infected patients.

In an exemplary implementation, generating the calibration dataset (step 101) may further include setting a severity borderline value between a set of $R_{CT}$ values associated with the second group and a set of $R_{CT}$ values associated with the third group based on clinical diagnosis and symptoms. The severity borderline value may include a highest value of $R_{CT}$ for a set of $R_{CT}$ values associated with the second group and also a lowest value of $R_{CT}$ for a set of $R_{CT}$ values associated with the third group. In an exemplary embodiment, the severity borderline value may include a $R_{CT}$ value of about 610Ω for COVID-19 infection. In an exemplary embodiment, the severity borderline value may include a $R_{CT}$ value of about 715Ω for COVID-19 infection.

Accordingly, in an exemplary embodiment, the generated calibration dataset may include a first set of $R_{CT}$ values versus a first set of total cytokines mass values, a second set of $R_{CT}$ values versus a second set of total cytokines mass values, and a third set of $R_{CT}$ values versus a third set of total cytokines mass values. The first set of $R_{CT}$ values may include $R_{CT}$ values being less than the threshold value representing no cytokine storm and no infection of the chronic inflammatory disease in the respective first group of persons. The second set of $R_{CT}$ values may include $R_{CT}$ values between the threshold value and the severity borderline value representing a moderate cytokine storm and moderate infection of the chronic inflammatory disease in the respective second group of persons. The third set of $R_{CT}$ values may include $R_{CT}$ values more than the severity borderline value representing a severe cytokine storm and severe infection of the chronic inflammatory disease in the respective third group of persons.

In an exemplary implementation, determining the level of total cytokines in the blood serum sample based on the calculated $R_{CT}$ (step 106 of methods 100 and 110) may further include grading a severity of the chronic inflammatory disease infection of the person. In an exemplary implementation, grading the severity of the chronic inflammatory disease infection of the person may include one of detecting the person being in a healthy (normal) state if the calculated $R_{CT}$ is within a first range of the calibration dataset including the first set of $R_{CT}$ values less than the threshold value, detecting the person being in a moderately infected state if the calculated $R_{CT}$ is within a second range of the calibration dataset including the second set of $R_{CT}$ values between the threshold value and the severity borderline value, and detecting the blood serum sample being in a severely infected state if the calculated $R_{CT}$ is within a third range of the calibration dataset including a third set of $R_{CT}$ values more than the severity borderline value.

In an exemplary implementation, generating the calibration dataset (step 101) may include generating the set of $R_{CT}$ values and generating the set of total cytokines mass values corresponding to the set of $R_{CT}$ values for a plurality of people with known status of a chronic inflammatory disease (CID) infection, for example, a plurality of people with known status of COVID-19 infection. In an exemplary embodiment, the plurality of people with known status of COVID-19 infection may include a first group of healthy persons, a second group of moderately COVID-19 infected patients, and a third group of severely COVID-19 infected patients.

In an exemplary embodiment, the calibration dataset may include three sets of data, including a first set, a second set, and a third set. The first set may include a first set of calculated $R_{CT}$ values for the first group of healthy persons respective to a first set of total cytokines mass values measured for the first group of healthy persons. In an exemplary embodiment, the first set of calculated $R_{CT}$ values may include $R_{CT}$ values less than a COVID-19-threshold value, and the first set of total cytokines mass values may include total cytokines mass values less than a COVID-19-reference value. The COVID-19-reference value may include an amount of total cytokines mass representing a cytokine storm. In an exemplary embodiment, the second set may include a second set of calculated $R_{CT}$ values for the second group of moderately COVID-19 infected patients respective to a second set of total cytokines mass values measured for the second group of moderately COVID-19 infected patients. In an exemplary embodiment, the second set of calculated $R_{CT}$ values may include $R_{CT}$ values more than the COVID-19-threshold value and less than a severity COVID-19-borderline $R_{CT}$ value. Correspondingly, the second set of total cytokines mass values may include total cytokines mass values between the COVID-19-reference value and a severity COVID-19-borderline total cytokines value. In an exemplary embodiment, the third set may include a third set of calculated $R_{CT}$ values for the third group of severely COVID-19 infected patients respective to a third set of total cytokines mass values measured for the third group of severely COVID-19 infected patients. In an exemplary embodiment, the third set of calculated $R_{CT}$ values may include $R_{CT}$ values more than the severity COVID-19-borderline $R_{CT}$ value. Correspondingly, the third set of total cytokines mass values may include total cytokines mass values more than the severity COVID-19-borderline total cytokines value.

In an exemplary implementation, determining the level of total cytokines in the blood serum sample based on the calculated $R_{CT}$ (step 106) may include detecting COVID-19 infection status of a person suspected to be infected with COVID-19. In an exemplary implementation, detecting the COVID-19 infection status of the person may include detecting the Covid-19 infection of the person if the calculated $R_{CT}$ is equal to or more than about 440Ω. In an exemplary implementation, detecting the COVID-19 infection status of the person may include detecting a healthy (normal) state for the person if the calculated $R_{CT}$ is less than about 340Ω, detecting a moderate COVID-19 infection of the person if the calculated $R_{CT}$ is between about 440Ω and about 610Ω, and detecting a severe COVID-19 infection of the person if the calculated $R_{CT}$ is more than about 715Ω.

It should be noted that all COVID-19 infected patients may suffer from a cytokine storm with total cytokines mass values more than the COVID-19-reference value. Moreover, severely COVID-19 infected patients may suffer from an intensive cytokine storm with total cytokines mass values more than the severity COVID-19-borderline total cytokines value. In an exemplary embodiment, the calculated $R_{CT}$ values may increase with increasing total cytokines mass values representing a COVID-19 infection and in some cases, a severity of COVID-19 infection. In an exemplary embodiment, the COVID-19-threshold value may include about 440Ω corresponding to the COVID-19-reference of about 7400 kDa, representing a border between the first group of healthy persons, and the second and third groups of COVID-19 infected patients. In an exemplary embodiment, the severity COVID-19-borderline $R_{CT}$ value may include about 715Ω corresponding to the COVID-19-reference of about 11600 kDa, representing a border between the second group of moderately COVID-19 infected patients and the third group of severely COVID-19 infected patients.

In an exemplary implementation, generating the calibration dataset (step 101) may further include generating (i.e., fitting or estimating) a mathematical relationship between the set of $R_{CT}$ values and the set of respective total cytokines mass values. In such implementation, determining the level of total cytokines in the blood serum sample based on the calculated $R_{CT}$ (step 106) may include calculating an amount of total cytokines in the blood serum sample utilizing the mathematical relationship between the set of $R_{CT}$ values and the set of respective total cytokines mass values.

In an exemplary embodiment, the relationship between the set of $R_{CT}$ values and the set of respective total cytokines mass values may be defined by:

$$TCM = (R_{CT} - 283.75)/0.0338 \qquad (Eq.\ 1)$$

where TCM is total cytokines mass of the blood serum sample (kDa), and $R_{CT}$ is the calculated $R_{CT}$ (Ω). In an exemplary embodiment, a cytokine storm for the person, and subsequently, a COVID-19 infection of the person may be detected in step 106 if the calculated TCM is equal to or more than a pre-determined value of total cytokines mass, for example, the COVID-19-reference of about 3000 kDa.

In an exemplary implementation, determining the level of total cytokines in the blood serum sample based on the calculated $R_{CT}$ (step 106 of methods 100 and 110) may further include diagnosing COVID-19 infection of the person if the calculated $R_{CT}$ is equal to or more than the COVID-19-threshold value.

Furthermore, determining the level of total cytokines in the blood serum sample based on the calculated $R_{CT}$ (step 106 of methods 100 and 110) may further include grading a severity of COVID-19 infection of the person based on the calculated $R_{CT}$. In an exemplary implementation, determining the level of total cytokines in the blood serum sample based on the calculated $R_{CT}$ (step 106 of methods 100 and 110) may include comparing the calculated $R_{CT}$ with the set of $R_{CT}$ values of the calibration dataset, detecting the person is in a healthy (normal) state if the calculated $R_{CT}$ is within the first set of the calibration dataset, detecting the person is in a moderately COVID-19 infected state if the calculated $R_{CT}$ is within the second set of the calibration dataset, and detecting the person is in a severely infected state if the calculated $R_{CT}$ is within the third set of the calibration dataset.

Figure 1C:
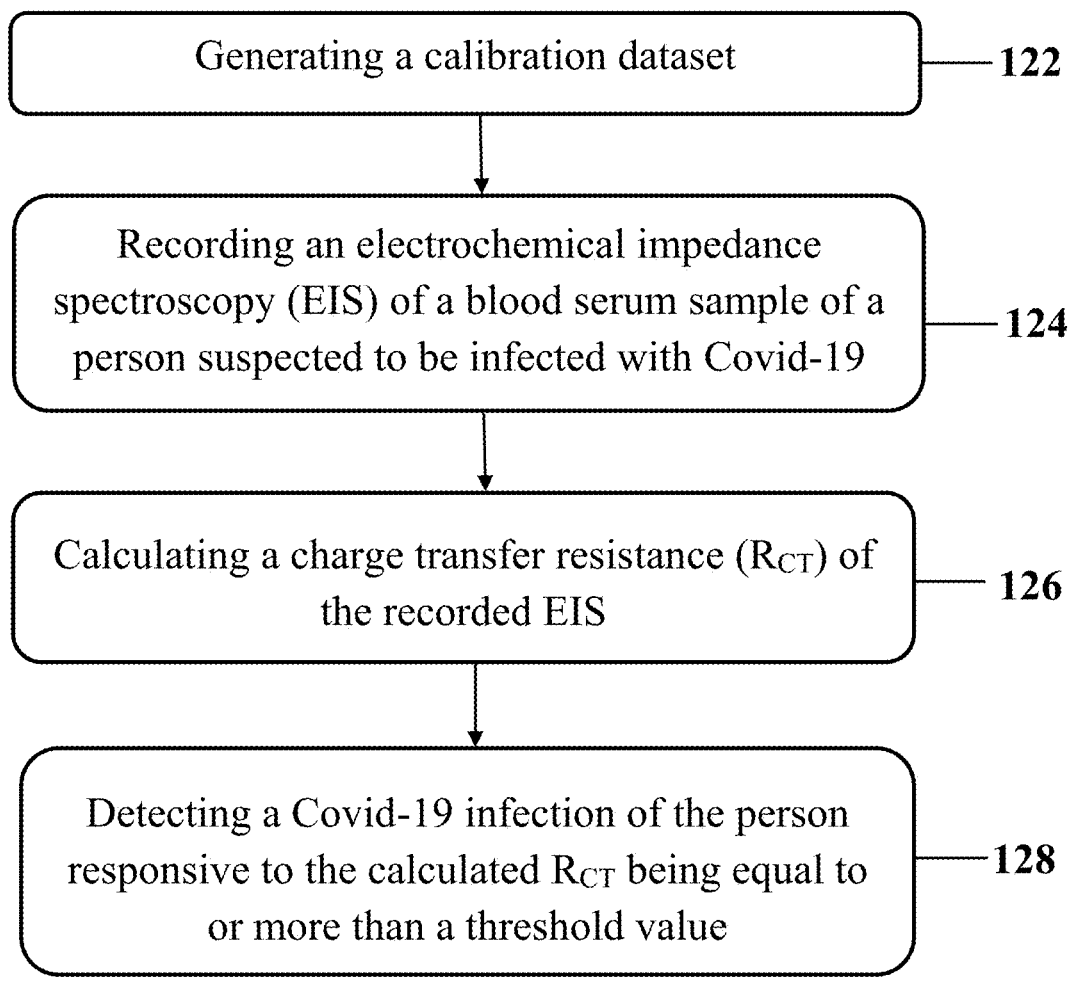
FIG. 1C shows an exemplary method for diagnosing COVID-19 infection of a person, consistent with one or more exemplary embodiments of the present disclosure.

According to exemplary embodiments described hereinabove, methods 100 and 110 may be utilized for diagnosing and grading COVID-19 infection of a person. FIG. 1C shows exemplary method 120 for diagnosing COVID-19 infection of a person, consistent with one or more exemplary embodiments of the present disclosure. Exemplary method 120 may include generating a calibration dataset including a set of total cytokines mass values respective to a set of $R_{CT}$ values (step 122 similar to step 101), recording an electrochemical impedance spectroscopy (EIS) of a blood serum sample of a person suspected to be infected with COVID-19 (step 124 similar to step 102), calculating a charge transfer resistance ($R_{CT}$) of the recorded EIS by measuring a diameter of a semicircular curved part of the recorded EIS (step 126 similar to step 104), and detecting a COVID-19 infection of the person responsive to the calculated $R_{CT}$ being equal to or more than a threshold value (step 128 similar to step 106).

In an exemplary implementation, determining the level of total cytokines in the blood serum sample based on the calculated $R_{CT}$ (step 106 of methods 100 and 110) may further include detecting a cytokine storm in the blood serum sample if the calculated $R_{CT}$ is more than the threshold value. In an exemplary implementation, determining the level of total cytokines in the blood serum sample based on the calculated $R_{CT}$ may include detecting the cytokine storm in the blood serum sample if the calculated $R_{CT}$ is more than about 440 corresponding to a total cytokines mass of more than about 7400 kDa. In an exemplary implementation, detecting the cytokine storm in the blood serum sample may include detecting an infection of a chronic inflammatory disease of a person associated with the blood serum sample whom the blood sample may be drawn from her. In an exemplary implementation, detecting the cytokine storm in the blood serum sample may include detecting a moderate infection of the chronic inflammatory disease of the person if the calculated $R_{CT}$ is between about 440Ω and about 610Ω. In an exemplary implementation, detecting the cytokine storm in the blood serum sample may include detecting a severe infection of the chronic inflammatory disease of the person if the calculated $R_{CT}$ is more than about 715Ω.

Example 1: Cytokine Analysis of Blood Serum Samples by ELISA Method

In this example, blood samples were collected from normal donators, moderately and severely infected patients (with signs of inflammatory diseases such as COVID-19) in three individual cohorts which were selected based on clinical judgments of the patients. An adequate volume of blood was sampled from normal donators and the patients and after serum isolation, cytokine measurement was performed by the ELISA method.

Although in hypercytokinemia many cytokines may be secreted into the blood, three key cytokines named Interleukin-6 (IL-6), Tumor Necrosis Factor-α (TNF-α) and Interferon-γ (IFN-γ) play more important role in cytokine storm relative to the others and show the most elevated levels in blood serum of the patients. On this basis, ELISA procedure was carried out to measure a number of produced cytokines by the immune system of each person.

In brief, known concentrations of recombinant human IL-6, TNF-α or INF-γ and experimental blood samples were added and incubated in polystyrene microtiter plates coated with an antibody against the appointed cytokine, followed by incubation with an enzyme-linked polyclonal antibody directed to the cytokine. Next, a substrate solution for the enzyme was added, and the color development was stopped by adding a solution of 2N $H_2SO_4$. The absorbance was measured with a microtiter plate spectrophotometer. An amount of IL-6, TNF-α, or INF-γ present in each blood sample was determined from a standard curve generated in each assay and expressed as picograms per milliliter. The sensitivity of the enzyme-linked immunosorbent assay for IL-6, TNF-α and INF-γ was 0.70 pg/ml, 1.88 pg/mL, and 8 pg/mL, respectively. The reproducibility of all measurements was within about 10%.

Figure 5A:
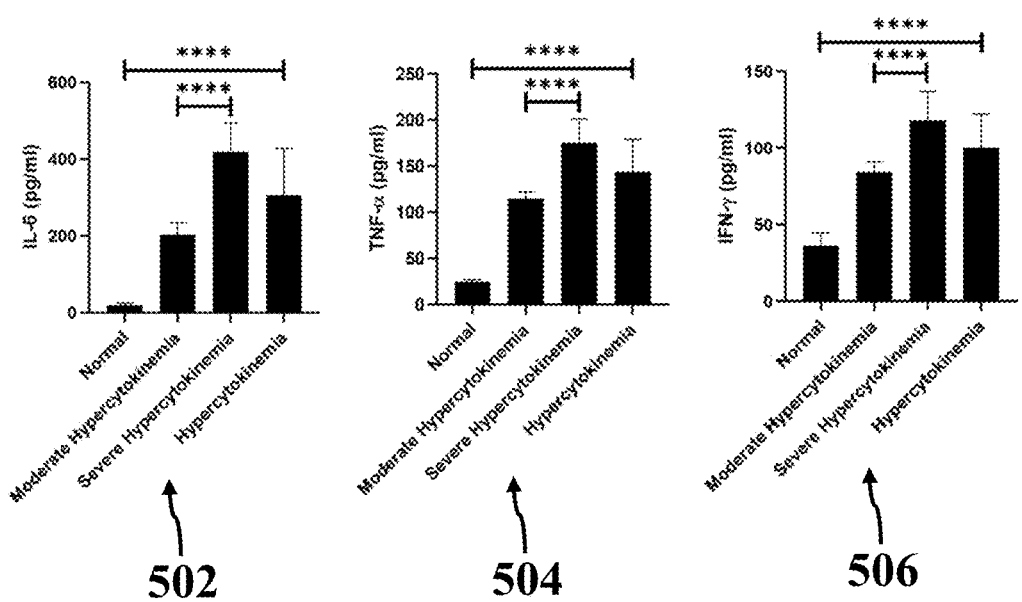
FIG. 5A shows comparing secreted levels of IL-6, TNF-α, and IFN-γ in blood serum of normal donors and patients with moderate and severe hypercytokinemia, consistent with one or more exemplary embodiments of the present disclosure.

FIG. 5A shows comparing secreted levels of IL-6 (graph 502), TNF-α (graph 504), and IFN-γ (graph 506) in the blood serum of normal donors and patients with moderate and severe hypercytokinemia, consistent with one or more exemplary embodiments of the present disclosure. It may be observed that the expressed levels of IL-6, TNF-α and IFN-γ cytokines in the infected patients were markedly higher than the normal group. Furthermore, analyzing the cytokines for the two groups of moderately and severely infected patients demonstrates a correlated secretion pattern of those three cytokines with the severity of the disease. Here, hypercytokinemia alone means sum of the moderate and severe cases.

Figure 5B:
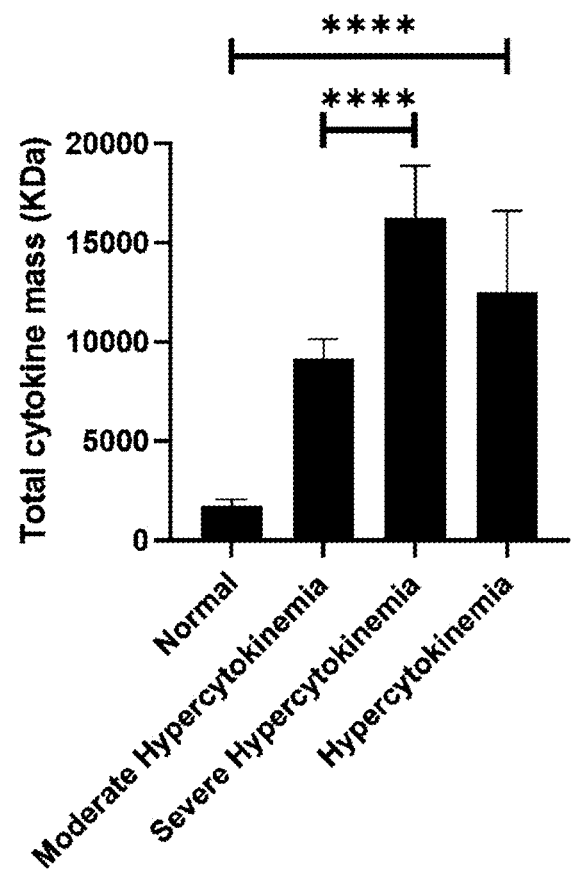
FIG. 5B shows comparing total cytokine mass in blood serum of normal donors and patients with moderate and severe hypercytokinemia, consistent with one or more exemplary embodiments of the present disclosure.

For more clarification, total molecular weight for all three types of cytokines were calculated for all patients including both normal and infected cases. To do this, for each person the amount of the expressed cytokine was multiplied by its molecular mass (IL-6: 23 kDa, TNF-α: 25 kDa and IFN-γ: 19 kDa) and summed for the all three cytokines. FIG. 5B shows comparing total cytokine mass in the blood serum of normal donors and patients with moderate and severe hypercytokinemia, consistent with one or more exemplary embodiments of the present disclosure. As presented in this figure, the total molecular weight of the mentioned cytokines for the suspicious COVID-19 patients was meaningfully increased as the stage of the disease becomes inferior.

Figure 6:
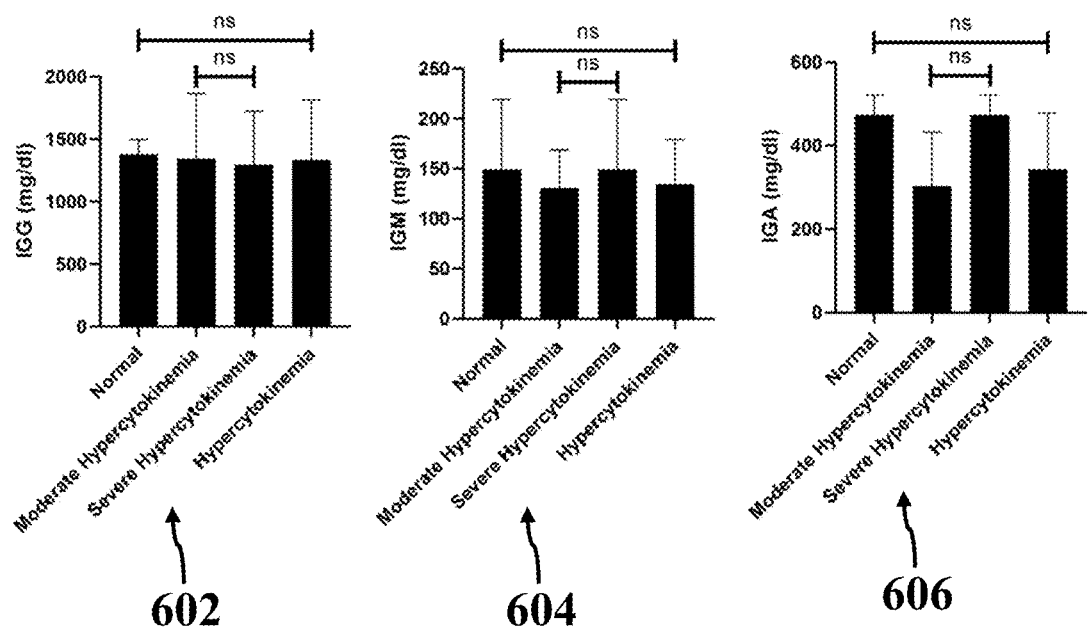
FIG. 6 shows comparing secreted levels of immunoglobulin G (IGG), immunoglobulin M (IGM), and immunoglobulin A (IGA) antibodies in blood serum of normal donors and patients with moderate and severe hypercytokinemia, consistent with one or more exemplary embodiments of the present disclosure.

Aside from the cytokine analysis, immunoglobulins G, M and A were also investigated for the normal and infected groups. FIG. 6 shows comparing secreted levels of immunoglobulin G (IGG) (graph 602), immunoglobulin M (IGM) (graph 604), and immunoglobulin A (IGA) (graph 606) antibodies in the blood serum of normal donors and patients with moderate and severe hypercytokinemia, consistent with one or more exemplary embodiments of the present disclosure. As may be seen, no meaningful correlation in the infected COVID-19 patients compared to the normal donors could be detected in the case of the IGG, IGM and IGA antibodies, while significant difference existed in the case of cytokines.

Figure 7:
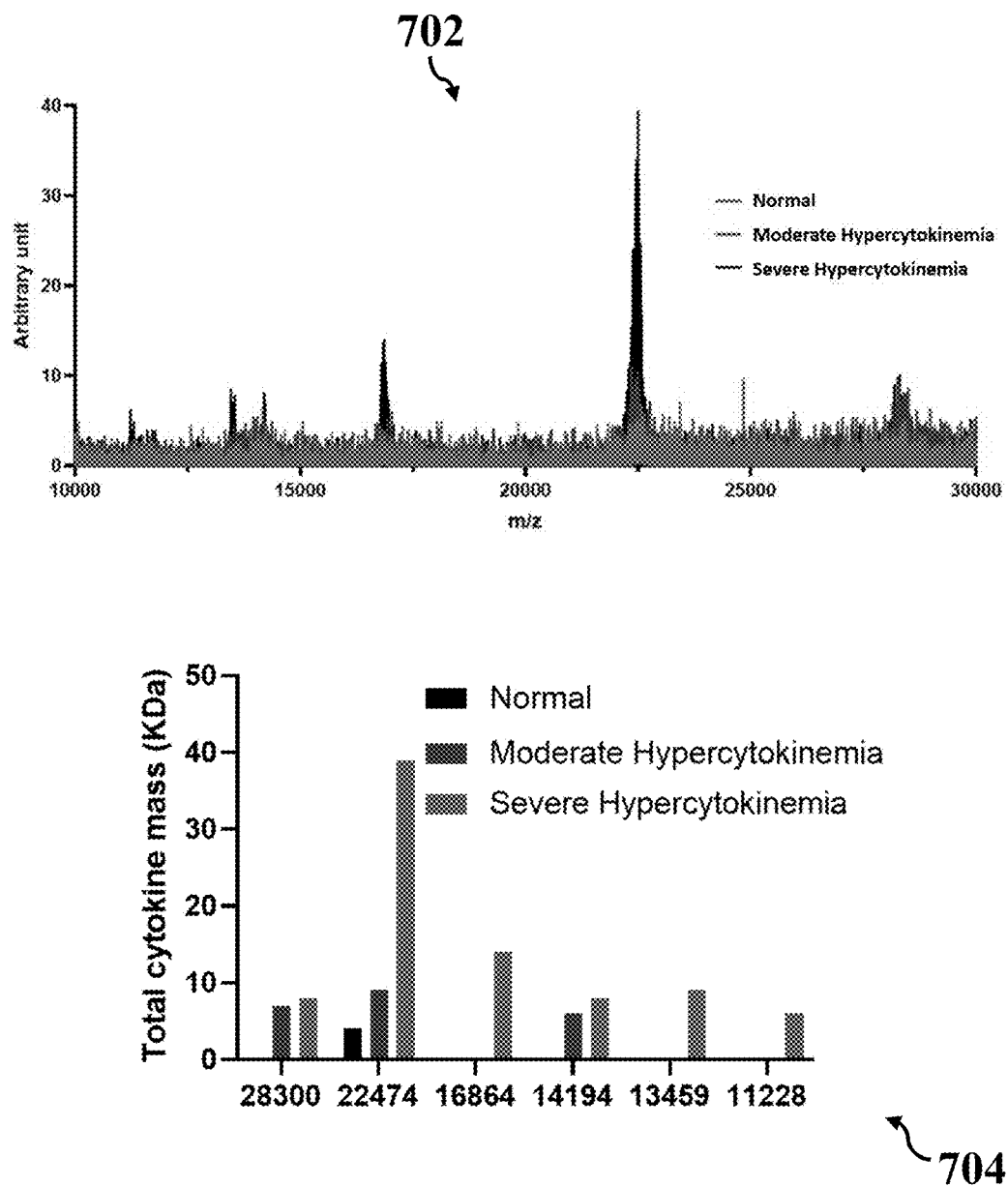
FIG. 7 shows an exemplary mass spectrum of blood serum of the three groups of normal, moderate and severe cytokine strom and an exemplary graph representing mass to charge (m/z) peaks and their abundance in the mass spectrum of the blood serums for the normal and hypercytokinemia groups, consistent with one or more exemplary embodiments of the present disclosure.

Moreover, mass spectroscopy (MS) analysis of plasma blood samples were analyzed by Matrix-assisted laser desorption/ionization (MALDI)-TOF mass spectrometry. For MS analysis, after diluting each sample up to 5 times and then ZipTip performing, the sample was spotted on MALDI plate and was mixed with alphacyano-4-hydroxy-cinnamic acid (CHCA) in 50% CAN containing 0.1% TFA (with 1:2 ratio) as a matrix solution. Then, the sample was air dried and analyzed in linear positive mode. FIG. 7 shows mass spectrum 702 of the blood serum of the three groups of normal, moderate and severe cytokine strom and graph 704 representing mass to charge (m/z) peaks and their abundance in the mass spectrum of the blood serums for the normal and hypercytokinemia groups, consistent with one or more exemplary embodiments of the present disclosure. The obtained mass spectrum revealed a total increase in intensity of mass peaks for the patients with severe symptoms and cytokine storm. Moreover, in some m/z such as 22474 which is close to the molecular weight of three mentioned cytokines, a meaningful increase may be observed in the mass peaks of normal samples (4) to severe patients (39). This might be in a well correlation with cytokine storm based tracing of people suspicious to COVID-19.

Example 2: Fabrication and Characterization of an Exemplary Biosensor

In this example, an exemplary biosensor similar to biosensor 300 was fabricated. At first, a bilayer of Au/Ti (30/5 nm) was deposited on top of a glass slide as a substrate using a sputtering system. Then, a circular pattern of three-electrode array of the biosensor was transferred to the substrate using a standard lithography method. Thereafter, a layer of graphene/Cu was placed and adhered on top of a working electrode of the three-electrode array. A sensing part of the three-electrode array was sealed by a holder; allowing for dropping a sample onto the sensing part inside the holder. The biosensor included an integrated three-electrode system including a circular working electrode with a diameter of about 5 mm, a counter electrode surrounding the circular working electrode and a reference electrode near both the circular working electrode and the counter electrode. A distance between working, reference and counter electrodes was about 1 mm. Sensing material of reference and counter electrodes were gold, and sensing material of the working electrode was a graphene monolayer on top of a copper substrate.

Figure 8:
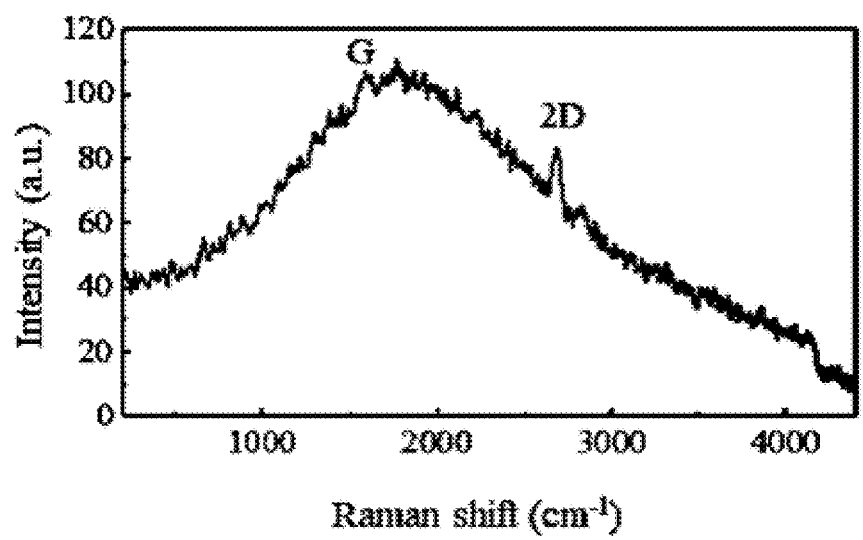
FIG. 8 shows a Raman spectrum of graphene/Cu of an exemplary working electrode of an exemplary fabricated biosensor, consistent with one or more exemplary embodiments of the present disclosure.

FIG. 8 shows a Raman spectrum of graphene/Cu of the working electrode of exemplary fabricated biosensor, consistent with one or more exemplary embodiments of the present disclosure. The Raman spectra shows two considerable peaks at 1562 $cm^{-1}$ and 2712 $cm^{-1}$ related to G-band (in-plane vibration mode) and 2D-band (double resonance scattering of inter-valley) of graphene layer, respectively. These peaks confirm the presence of graphene layer on Cu.

As observed in Raman spectrum, there is not significant D-band peak in diagram, which illustrates approximately no-defects on graphene.

Figure 9:
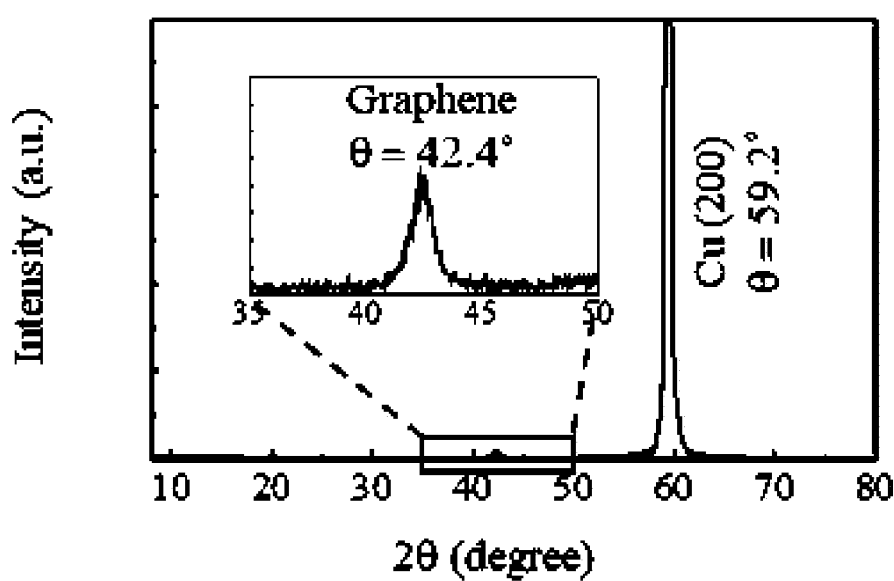
FIG. 9 shows exemplary X-ray diffraction analysis (XRD) analysis of graphene/Cu of an exemplary working electrode of an exemplary fabricated biosensor, consistent with one or more exemplary embodiments of the present disclosure.

Formation of graphene/Cu was also investigated by X-ray diffraction (XRD) technique. FIG. 9 shows XRD analysis of graphene/Cu of the working electrode of exemplary fabricated biosensor, consistent with one or more exemplary embodiments of the present disclosure. A sharp diffraction peak at 59.2° is related to Cu with plane of (200). Also, a tiny peak at 42.4° corresponds to the graphene layer.

Figure 10:
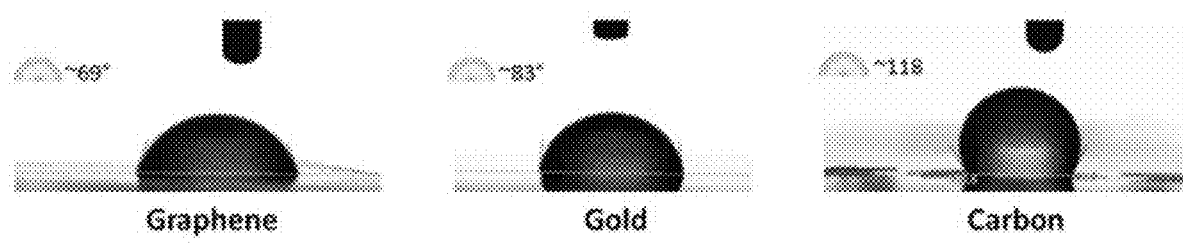
FIG. 10 shows contact angle comparison of a normal blood serum sample over graphene, gold, and carbon substrates, consistent with one or more exemplary embodiments of the present disclosure.

It should be noted that a material that may be chosen for depositing on surface of electrodes to interact with a blood serum sample, may play a significant role in accuracy and validity of electrical responses acquired from exemplary fabricated biosensor. Accordingly, three types of electrode materials including gold (Au), carbon, and graphene were investigated as candidates for EIS analysis. Adhesion and spread of a blood serum sample on the selected substrates were evaluated by contact angle method. As the water composes the most part of the blood serum sample, the blood serum sample may have more tendency to hydrophilic substrates. FIG. 10 shows contact angle comparison of a normal blood serum sample over graphene, gold and carbon substrates, consistent with one or more exemplary embodiments of the present disclosure. It may be observed that the maximum contact angle was attributed to the carbon surface with about 118° and the minimum was for graphene electrode with angle of about 69°. The results may demonstrate that the blood serum is mostly attracted to the graphene-coated electrode rather than the Au and carbon.

Example 3: Derivation of $R_{CT}$ in Human Blood Serum Samples

Patients suspicious to be infected by SARS-CoV-2 virus was selected based on the severity of the disease. The presence and severity of the disease was reported based on the symptoms and clinical exams of the patients presented in latest guidelines for clinical management of COVID-19 patients published by WHO. The serum samples were prepared from the residues of patients' and candidates' blood who did serological test to check themselves. When the blood was sampled and coagulated, the serum was isolated from the whole blood by centrifugation. Human blood samples from normal and suspicious patients were collected and then divided into clot activator tubes. For serum isolation, the clot activator tubes were maintained at 37° C. for 15 minutes and then centrifuged for about 10 min at about 3000 rpm. Serum sample as a top part of the centrifuged liquid samples was extracted for EIS measurements. For EIS analysis, the serum was mixed in a ratio of about 3:1 with an electrolyte solution (0.1 M KCl, 5 mM $K_3[Fe(CN)_6]$ and 5 mM $K_4[Fe(CN)_6]$). Then, about 200 µL of the produced mixture was added to an exemplary three-electrode biosensor similar to biosensor 300. EIS was performed using a potentiostat for a potential amplitude of about 10 mV and in a frequency range of about 10 mHz to 100 KHz. Charge transfer resistance ($R_{CT}$) was calculated based on the Nyquist diagram for each sample. Finally, the $R_{CT}$ was compared between the cases without sign of cytokine storm and those who have hypercytokinemia based on the obtained results utilizing the ELISA method according to EXAMPLE 1 hereinabove.

Figure 11A:
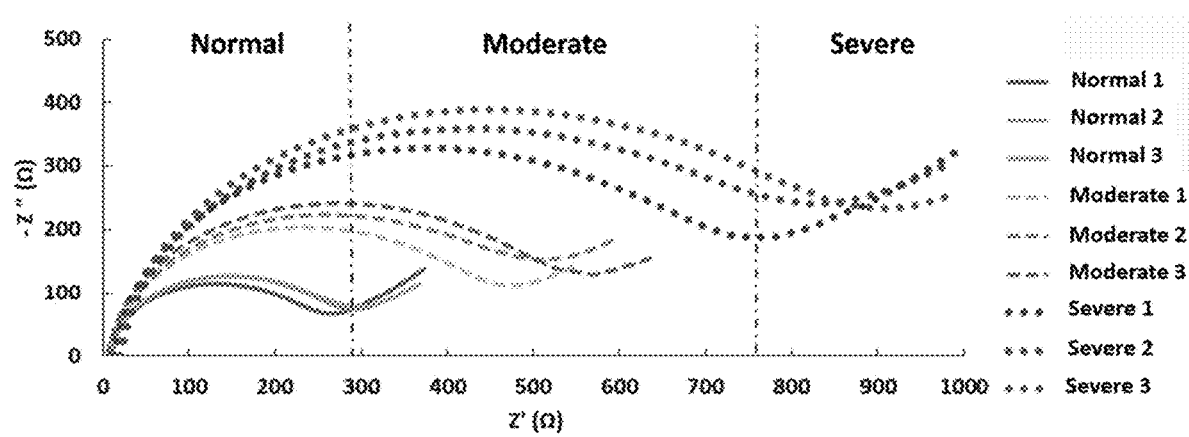
FIG. 11A shows an exemplary Nyquist plot for 9 samples of blood serum for each group of normal, moderate, and severely infected patients, consistent with one or more exemplary embodiments of the present disclosure.
Figure 11B:
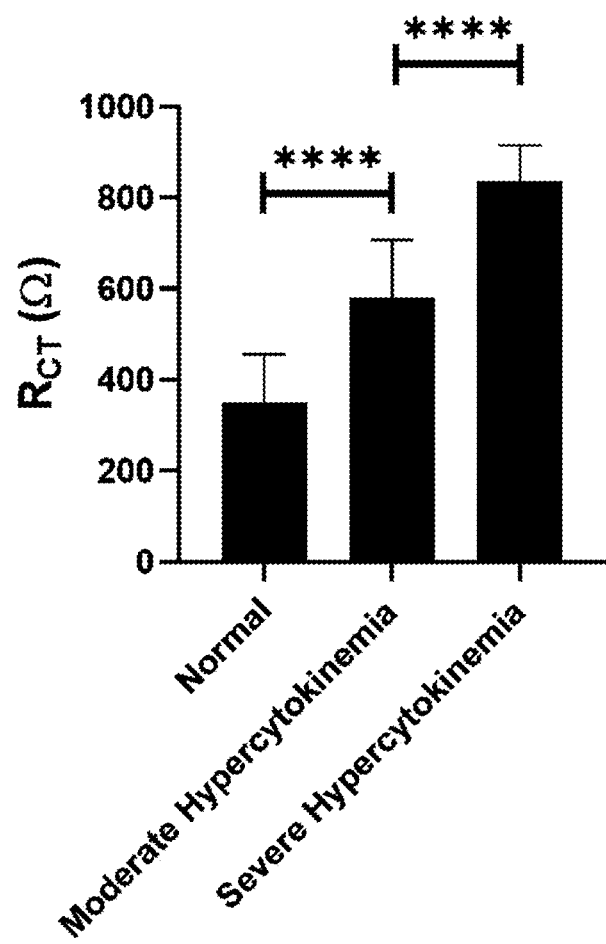
FIG. 11B shows comparing average values of charge transfer resistance ($R_{CT}$) for three groups of group of normal, moderate, and severely infected patients, consistent with one or more exemplary embodiments of the present disclosure.

FIG. 11A shows Nyquist plot for 9 samples of blood serum for each group of normal, moderate, and severely infected patients, consistent with one or more exemplary embodiments of the present disclosure. This figure demonstrates the obtained Nyquist plot for the serums of normal people without any symptoms and patients suspicious to the COVID-19 disease. Three levels of responses with distinct curves may be observed in this figure. Smallest curves were recorded for normal donators and largest curves were observed in the EIS responses of the patients with severe infection. FIG. 11B shows comparing average values of $R_{CT}$ for three groups of group of normal, moderate, and severely infected patients, consistent with one or more exemplary embodiments of the present disclosure. As could be deduced from this figure, a semicircle diameter of Nyquist plots in FIG. 11A as an indicator of the $R_{CT}$ for normal groups and different stages of the patients showed meaningful ranges.

Figure 12A:
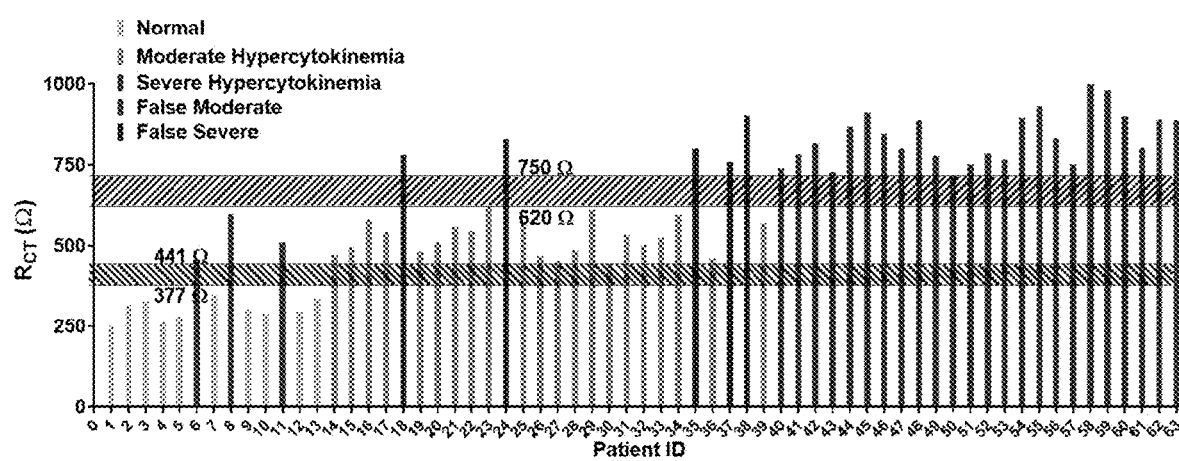
FIG. 12A shows $R_{CT}$ values for 63 individual normal persons and infected patients, consistent with one or more exemplary embodiments of the present disclosure.
Figure 12B:
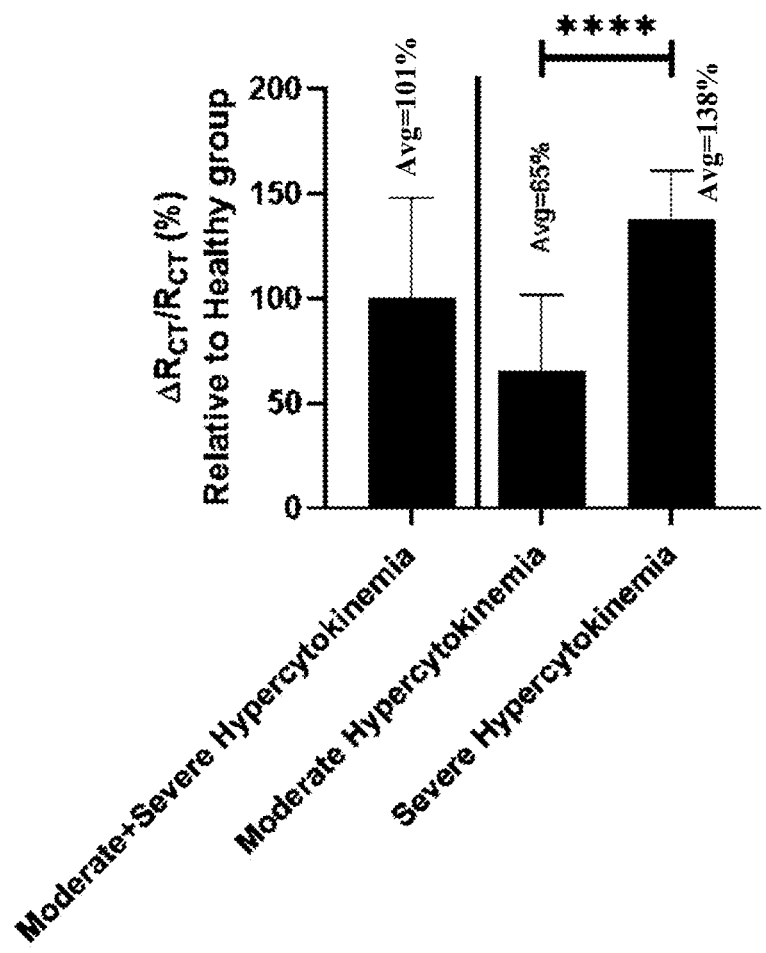
FIG. 12B shows increase percentage of $R_{CT}$ for COVID-19 patients in different progression stages relative to an avergae value of normal group, consistent with one or more exemplary embodiments of the present disclosure.

FIG. 12A shows $R_{CT}$ values for 63 individual normal persons and infected patients, consistent with one or more exemplary embodiments of the present disclosure. It may be observed that $R_{CT}$ for all of normal serum samples is less than about 377Ω while for the moderate cases stand in a range of about 441Ω to about 620Ω and severe ones are more than about 750Ω. Ranges from about 377Ω to about 441Ω and about 620Ω to about 750Ω may be free bands between normal-moderate and moderate-severe groups, respectively. The results of the impedimetric analysis showed an increasing correlation between $R_{CT}$ (dielectric properties of blood serum) and the disease from infection to progression in stage. Lowest $R_{CT}$ was recorded from samples of normal people while highest $R_{CT}$ was recorded from samples of severely infected patients. FIG. 12B shows increase percentage of $R_{CT}$ for COVID-19 patients in different progression stages relative to an avergae value of normal group, consistent with one or more exemplary embodiments of the present disclosure. An average increase (% $\Delta R_{CT}/R_{CT}$) of about 101% was observed for the infected patients compared to the normal donators. Such a value of % $\Delta R_{CT}/R_{CT}$ for moderate and severe cases were about 65% and about 138%, respectively.

Figure 13B:
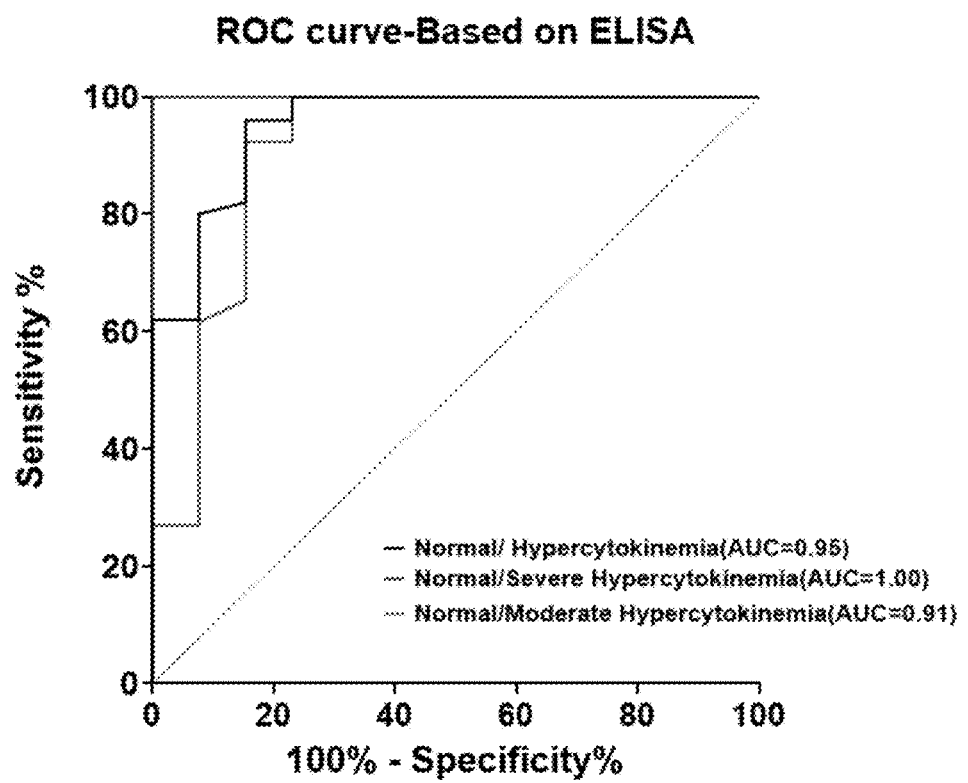
FIG. 13B shows exemplary receiver operating characteristic curve (ROC) curves for comparing EIS analysis with ELISA technique on detection of cytokine storm, consistent with one or more exemplary embodiments of the present disclosure.

To assess a correlation of hypercytokinemia with the increased charge transfer resistance obtained by the EIS, Receiver-Operating Characteristic (ROC) analysis was performed. Gold standard for positively scoring a patient with cytokine storm was ELISA tests (according to EXAMPLE 1) from the three cytokines of IL-6, TNF-α and IFN-γ and evaluating the total cytokine mass. FIG. 13A shows confusion matrix of diagnostic results obtained by EIS analysis and ELISA method for 63 persons, consistent with one or more exemplary embodiments of the present disclosure. FIG. 13B shows ROC curves for comparing EIS analysis with ELISA technique on detection of cytokine storm, consistent with one or more exemplary embodiments of the present disclosure. The statistical analysis shows a sensitivity of 100% and specificity of 77% with AUC of 0.95 for the biosensor with respect to the ELISA as the gold standard for cytokine measurement. It is worth to note that a sum of the moderate and severe cases was studied for the ROC analysis.

Figure 14:
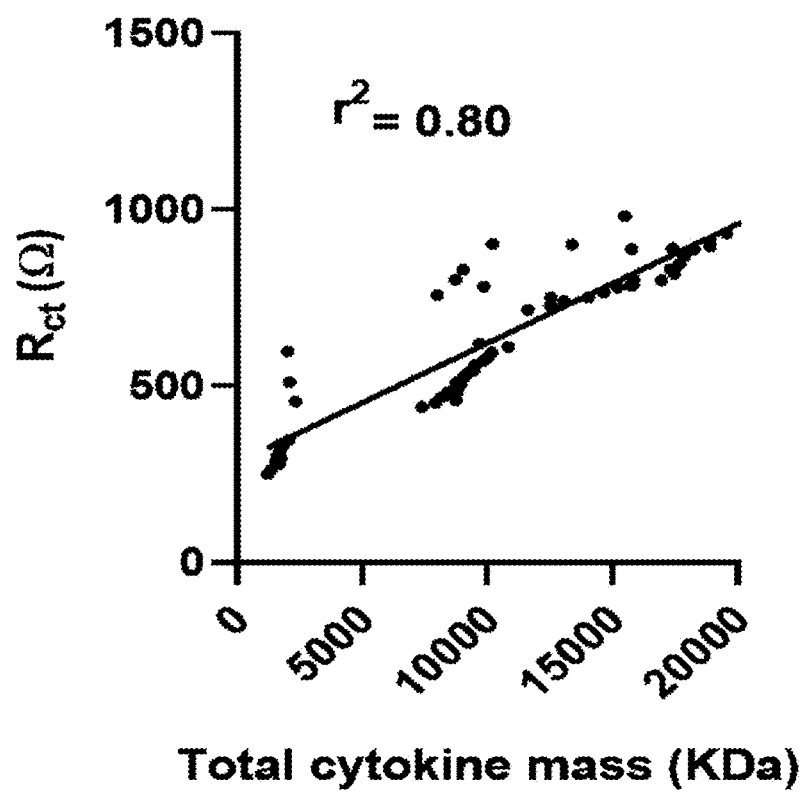
FIG. 14 shows a calibration curve based on measured $R_{CT}$ values and total cytokines mass for three groups of normal, moderate, and severe cases, consistent with one or more exemplary embodiments of the present disclosure.

Moreover, a calibration curves for the obtained $R_{CT}$ values versus total cytokine mass measured according to EXAMPLE 1, were plotted. FIG. 14 shows a calibration curve based on measured $R_{CT}$ values and total cytokines mass for all three groups of normal, moderate and severe cases, consistent with one or more exemplary embodiments of the present disclosure. In this figure, dots illustrates the charge transfer resistance data, whereas the line is corresponding data fitting results on the basis of simple linear regression method. Based on the curves, there may be a satisfactory linear relationship with $r^2=0.80$ between the $R_{CT}$ and the total mass of the cytokines. Total cytokine mass for the patients was between 7395 to 20770 kDa while this value for the normal group was between 1206 to 2345 kDa. Also, this value in moderate patients was about half of that in severe cases (FIG. 5B).

Figure 15:
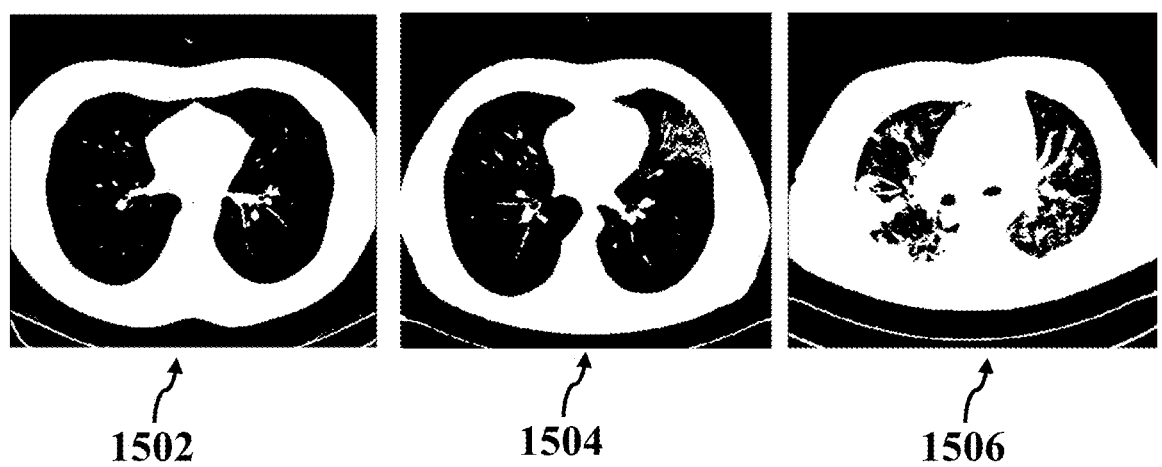
FIG. 15 shows exemplary CT scan images of three exemplary persons from three groups of normal, moderate, and severe cases, consistent with one or more exemplary embodiments of the present disclosure.

Example 4: Evaluating the Capability of the Biosensor for COVID-19 Detection In this example, capability of the fabricated biosensor similar to biosensor 300 and utilized by an exemplary method similar to method 120 as described in above examples was investigated for detecting patients with COVID-19 disease since a cytokine storm may be an evidenced consequence in most of the COVID-19 patients. Gold standard for positively scoring a COVID-19 infected patient was either RT-PCR or CT-Scan. FIG. 15 shows exemplary CT images of three exemplary persons from three groups of normal, moderate, and severe cases, consistent with one or more exemplary embodiments of the present disclosure. Exemplary chest CT image 1502 of a normal lung (ID #4) shows no abnormal opacification while for a moderate case shown in image 1504, glass-ground opacification (GGO) may be seen in both lobes of lung (ID #29). Such a bilateral GGO pattern in severe cases may be more intensive with more involved area of both lung lobes accompanied with consolidation as shown for patient ID #55 in image 1506.

Figure 16C:
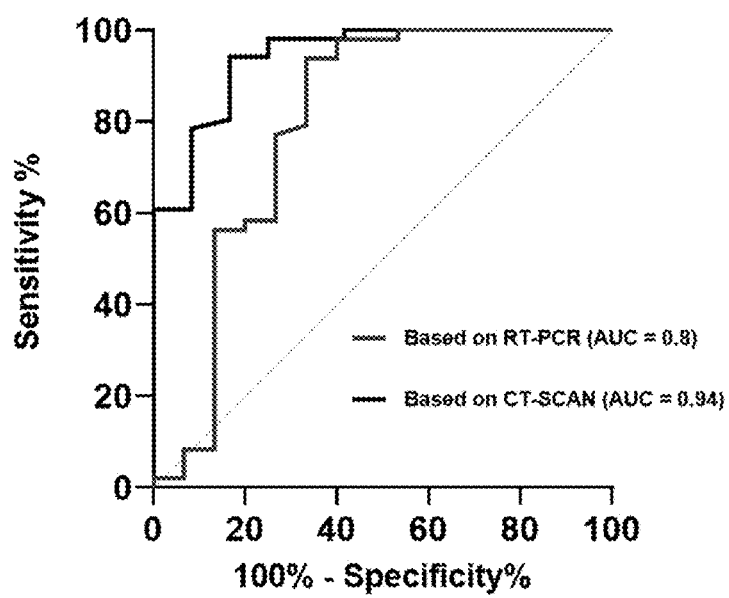
FIG. 16C shows ROC curves for comparing EIS analysis with RT-PCR and CT scan techniques on detection of cytokine storm, consistent with one or more exemplary embodiments of the present disclosure.

Table 1 compares detailed data of 63 persons analyzed by EIS sensor, RT-PCR, CT-Scan and cytokine analyses. As presented, three of patients (ID #23, ID #59, and ID #60) with clinical symptoms of infection were also analyzed in a case of cytokine storm as well as their CT/PCR results. Interestingly, their $R_{CT}$ value was placed in range of severely infected patients with CT involvement but the RT-PCR showed no signs of COVID-19 infection and diagnosis of acute Flu was more probable. On the other hand, $R_{CT}$ for three cases (ID #6, ID #8, and ID #11) were in range of moderately infected patients, while CT/PCR was negative and no cytokine storm was detected by the ELISA results. These false signals of EIS for such cases might be due to an unknown non-specific binding of other elevated reagents in the blood serum of tested patients. Moreover, four false negatives were recorded by EIS analysis with normal RT-PCR and chest CT results (ID #3, ID #7, ID #9, and ID #13). The blood analysis of these patients revealed non-elevated IL-6, TNF-α and IFN-γ cytokines which indicated that the immune system was not reacted to the virus yet and just the lungs were involved in the infection. Hence, no cytokine storm was happened and neither ELISA nor EIS diagnosed the COVID-19 disease. In case of COVID-19 detection, about 92% of sensitivity with respect to both CT/PCR, 67% and 50% of specificity as well as AUC of 0.91 and 0.73 was reached based on CT and RT-PCR methods, as shown respectively in FIGS. 16A, 16B, and 16C. FIG. 16A shows confusion matrix of diagnostic results obtained by EIS analysis and RT-PCR method for 63 persons, consistent with one or more exemplary embodiments of the present disclosure. FIG. 16B shows confusion matrix of diagnostic results obtained by EIS analysis and CT scan method for 63 persons, consistent with one or more exemplary embodiments of the present disclosure. FIG. 16C shows ROC curves for comparing EIS analysis with RT-PCR and CT scan techniques on detection of cytokine storm, consistent with one or more exemplary embodiments of the present disclosure.

TABLE 1

EIS, CT, RT-PCR and total cytokine mass results of normal and COVID-19 patients

| Patient ID | $R_{CT}$ | $\Delta R_{CT}/R_{CT}$ (Avg) % | CT scan | RT-PCR | Total cytokine mass (kDa) |
|---|---|---|---|---|---|
| 1 | 250 | — | ☒ | ☒ | 1206.46 |
| 2 | 315 | — | ☒ | ☒ | 1710.1 |
| 3 | 328 | — | ☑ | ☑ | 1806.7 |
| 4 | 263 | — | ☒ | ☒ | 1367.5 |
| 5 | 278 | — | ☒ | ☒ | 1665.4 |
| 6 | 456 | 29.9 | ☒ | ☒ | 2345.4 |
| 7 | 347 | — | ☑ | ☑ | 2073.4 |
| 8 | 598 | 70.37 | ☒ | ☒ | 2010.7 |
| 9 | 301 | — | ☑ | ☑ | 1614 |
| 10 | 288 | — | ☒ | ☒ | 1556.8 |
| 11 | 510 | 45.3 | ☒ | ☒ | 2090.6 |
| 12 | 294 | — | ☒ | ☒ | 1753.6 |
| 13 | 336 | — | ☑ | ☑ | 1756.9 |
| 14 | 472 | 34.47 | ☑ | ☑ | 8326 |
| 15 | 495 | 41.02 | ☑ | ☑ | 8715 |
| 16 | 582 | 65.8 | ☑ | ☑ | 10046 |
| 17 | 542 | 54.41 | ☑ | ☑ | 9368 |
| 18 | 780 | 122.2 | ☑ | ☑ | 9852 |
| 19 | 481 | 37.03 | ☑ | ☑ | 8412 |
| 20 | 510 | 45.29 | ☑ | ☑ | 8760 |
| 21 | 559 | 59.25 | ☑ | ☑ | 9523 |
| 22 | 544 | 54.98 | ☑ | ☑ | 9437 |
| 23 | 620 | 76.63 | ☑ | ☒ | 9682 |
| 24 | 829 | 136.18 | ☑ | ☑ | 9036 |
| 25 | 571 | 62.67 | ☑ | ☑ | 9818 |
| 26 | 467 | 33.04 | ☑ | ☑ | 8113 |
| 27 | 452 | 28.77 | ☑ | ☑ | 7910 |
| 28 | 486 | 38.46 | ☑ | ☑ | 8798 |
| 29 | 610 | 73.79 | ☑ | ☑ | 10822 |
| 30 | 441 | 25.64 | ☑ | ☑ | 7395 |
| 31 | 535 | 52.42 | ☑ | ☑ | 9209 |
| 32 | 503 | 43.30 | ☑ | ☑ | 8899 |
| 33 | 526 | 49.85 | ☑ | ☑ | 9100 |
| 34 | 596 | 69.80 | ☑ | ☑ | 10178 |
| 35 | 800 | 127.92 | ☑ | ☑ | 8724 |
| 36 | 459 | 30.77 | ☑ | ☑ | 8743 |
| 37 | 758 | 115.95 | ☑ | ☑ | 7997 |
| 38 | 902 | 156.98 | ☑ | ☑ | 10200 |
| 39 | 570 | 62.4 | ☑ | ☑ | 9826 |
| 40 | 740 | 110.82 | ☑ | ☑ | 13062 |
| 41 | 784 | 123.36 | ☑ | ☑ | 15712 |
| 42 | 818 | 133.05 | ☑ | ☑ | 17462 |
| 43 | 728 | 107.4 | ☑ | ☑ | 12524 |
| 44 | 867 | 147 | ☑ | ☑ | 17866 |
| 45 | 911 | 159.54 | ☑ | ☑ | 18907 |
| 46 | 845 | 140.74 | ☑ | ☑ | 17689 |
| 47 | 799 | 127.63 | ☑ | ☑ | 16949 |
| 48 | 887 | 152.7 | ☑ | ☑ | 18251 |
| 49 | 778 | 121.65 | ☑ | ☑ | 15201 |
| 50 | 715 | 103.7 | ☑ | ☑ | 11620 |
| 51 | 750 | 113.67 | ☑ | ☑ | 12534 |
| 52 | 786 | 123.93 | ☑ | ☑ | 15833 |
| 53 | 765 | 117.95 | ☑ | ☑ | 14644 |
| 54 | 896 | 155.27 | ☑ | ☑ | 18901 |
| 55 | 932 | 165.52 | ☑ | ☑ | 19573 |
| 56 | 831 | 136.75 | ☑ | ☑ | 17321 |
| 57 | 751 | 113.96 | ☑ | ☑ | 14015 |
| 58 | 1003 | 185.75 | ☑ | ☑ | 20770 |
| 59 | 980 | 179.2 | ☑ | ☒ | 15493 |
| 60 | 900 | 156.41 | ☑ | ☒ | 13401 |
| 61 | 802 | 128.49 | ☑ | ☑ | 15840 |
| 62 | 890 | 153.56 | ☑ | ☑ | 17411 |
| 63 | 888 | 152.99 | ☑ | ☑ | 15768 |

Table 2 shows descriptive comparison on performance of cytokine storm and COVID-19 detection between exemplary method based on EIS analysis and ELISA, CT, and RT-PCR methods. These outcomes may mean that exemplary method based on EIS analysis and exemplary biosensor strongly responses to the patients with cytokine storm activity in their blood serum not affected by type of disease. So, exemplary method based on EIS analysis may compete with the current ELISA method on detection of the cytokine storm in the serum samples due to remarkable features of exemplary method and biosensor. In addition, since most of the patients infected with COVID-19 disease suffer from the cytokine storm, hence the results of EIS-based method on diagnosis of the infected patients by SARS-CoV-2 virus seems acceptable and could be compared with current methods of diagnosis such as RT-PCR and CT scan.

TABLE 2

Descriptive comparison on performance of cytokine storm and COVID-19 detection between EIS analysis and ELISA, CT, and RT-PCR methods

| Method | Sample | Time | Accuracy | Cost | Procedure |
|---|---|---|---|---|---|
| Comparing methods for cytokine storm detection | | | | | |
| ELISA | Serum | <90 min | High | Low-Cost | Simple |
| Our Method | Serum | <10 min | High | Low-Cost | Simple |
| Comparing methods for COVID-19 detection | | | | | |
| CT scan | Lung | <15 s | High | Expensive | Simple |
| RT-PCR | Saliva | <3 h | High | Expensive | Complex |
| Our Method | Serum | <10 min | Medium | Low-Cost | Simple |

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for diagnosing COVID-19 infection, comprising: drawing a blood sample from a person suspected to be infected with COVID-19 virus; separating a blood serum sample from the blood sample by centrifuging the blood sample;
   forming a mixture by mixing the blood serum sample with an electrolyte solution comprising a solution of at least one metal ion; putting the mixture in contact with three-integrated electrodes of a biosensor; and recording the EIS of the mixture in contact with the three-integrated electrodes using an electrochemical stimulator-analyzer, and
   recording an electrochemical impedance spectroscopy (EIS) associated with the blood serum sample;
   calculating a charge transfer resistance ($R_{CT}$) of the recorded EIS by measuring a diameter of a semicircular curved part of the recorded EIS; and detecting a COVID-19 infection status of the person based on the calculated $R_{CT}$ if the calculated $R_{CT}$ is equal to or more than a threshold value.

2. The method of claim 1, wherein detecting the COVID-19 infection status of the person comprises:

detecting a healthy (normal) state for the person if the calculated $R_{CT}$ is less than 340Ω;

detecting a moderate COVID-19 infection of the person if the calculated $R_{CT}$ is between 440Ω and 610Ω; and detecting a severe COVID-19 infection of the person if the calculated $R_{CT}$ is more than 715 Ω.

3. The method of claim 1, further comprising generating a calibration dataset, comprising:

generating a set of $R_{CT}$ values, comprising:

recording a set of EIS plots from a respective plurality of blood serum samples drawn from a corresponding plurality of persons; and calculating the set of $R_{CT}$ values respective to the set of recorded EIS plots by measuring a diameter of a semicircular curved part of each of the recorded EIS plots; and generating a set of total cytokine mass values corresponding to the set of $R_{CT}$ values by measuring total cytokines mass of each of the plurality of blood serum samples utilizing a cytokine measurement assay.

4. The method of claim 3, wherein detecting the COVID-19 infection status of the person based on the calculated $R_{CT}$ comprises:

comparing the calculated $R_{CT}$ with the set of $R_{CT}$ values of the calibration dataset;

detecting the person is in a healthy (normal) state if the calculated $R_{CT}$ is within a first range of the calibration dataset, the first range of the calibration dataset comprising a first set of $R_{CT}$ values less than the threshold value, the first set of $R_{CT}$ values measured from a group of healthy people;

detecting the person is in a moderately COVID-19 infected state if the calculated $R_{CT}$ is within a second range of the calibration dataset, the second range of the calibration dataset comprising a second set of $R_{CT}$ values between the threshold value and a severity borderline value, the second set of $R_{CT}$ values measured from a group of moderately infected patients with COVID-19; and detecting the person is in a severely infected state if the calculated $R_{CT}$ is within a third range of the calibration dataset, the third range of the calibration dataset comprising a third set of $R_{CT}$ values more than the severity borderline value, the third set of $R_{CT}$ values measured from a group of severely infected patients with COVID-19.

5. The method of claim 1, wherein detecting the COVID-19 infection of the person comprises detecting the COVID-19 infection of the person if the calculated $R_{CT}$ is equal to or more than 440Ω.

6. The method of claim 1, wherein recording the EIS from the mixture in contact with the three-integrated electrodes comprises recording the EIS of the mixture in contact with the three-integrated electrodes at an AC potential amplitude between 5 mV and 20 mV while sweeping a frequency range between 0.01 Hz and 100 kHz.

7. The method of claim 1, wherein the electrochemical stimulator-analyzer comprises a potentiostat.

8. The method of claim 1, wherein putting the mixture in contact with the three-integrated electrodes of the biosensor comprises dropping the mixture on a surface of three-integrated electrodes of the biosensor, the three-integrated electrodes comprising: a working electrode comprising a circular-shaped sensing part, the circular-shaped sensing part comprising a bilayer of graphene/copper adhered on a first bilayer of gold/titanium (Au/Ti) deposited on a substrate, the working electrode configured to be an attachment site for the mixture; a counter electrode comprising a partially annular part placed around the working electrode, the counter electrode comprising a second bilayer of Au/Ti deposited on the substrate, the counter electrode configured to acquire the electrical response from the working electrode; and a reference electrode placed adjacent to both the working electrode and the counter electrode, the reference electrode comprising a third bilayer of Au/Ti deposited on the substrate, the reference electrode configured to adjust a specific voltage between the working and the counter electrodes.

9. The method of claim 8, wherein the bilayer of graphene/copper comprises a layer of graphene sheets with a thickness between 0.1 nm and 1 nm deposited on a layer of copper with a thickness between 1 μm and 30 μm.

10. The method of claim 8, wherein each of the bilayers of Au/Ti comprises a layer of gold with a thickness between 10 nm and 50 nm deposited on a layer of titanium with a thickness between 3 nm and 10 nm.

11. The method of claim 8, wherein the substrate comprises at least one of a glass substrate, a silicon substrate, a ceramic substrate, and combinations thereof.

12. A method for measuring a level of total cytokines in a blood serum sample, comprising:

recording an electrochemical impedance spectroscopy (EIS) associated with the blood serum sample;

calculating a charge transfer resistance ($R_{CT}$) of the recorded EIS by measuring a diameter of a semicircular curved part of the recorded EIS; and determining the level of total cytokines in the blood serum sample based on the calculated $R_{CT}$ by looking up the calculated $R_{CT}$ in a calibration dataset comprising a set of total cytokine mass values respective to a set of $R_{CT}$ values.

13. The method of claim 12, further comprising generating the calibration dataset, comprising:

generating the set of $R_{CT}$ values, comprising:

recording a set of EIS plots from a respective plurality of blood serum samples drawn from a corresponding plurality of persons; and calculating the set of $R_{CT}$ values respective to the set of recorded EIS plots by measuring a diameter of a semicircular curved part of each of the recorded EIS plots; and generating the set of total cytokine mass values corresponding to the set of $R_{CT}$ values by measuring total cytokines mass of each of the plurality of blood serum samples utilizing a cytokine measurement assay.

14. The method of claim 12, wherein determining the level of total cytokines in the blood serum sample based on the calculated $R_{CT}$ further comprises diagnosing an infection of a chronic inflammatory disease (CID), comprising:

detecting the infection of the chronic inflammatory disease for a person associated with the blood serum sample responsive to the calculated $R_{CT}$ being more than a threshold value.

15. The method of claim 14, wherein determining the level of total cytokines in the blood serum sample based on the calculated $R_{CT}$ further comprises grading a severity of the chronic inflammatory disease infection of the person, comprising:

detecting the person is in a healthy (normal) state if the calculated $R_{CT}$ is within a first range of the calibration dataset, the first range of the calibration dataset comprising a first set of $R_{CT}$ values less than the threshold value, the first set of $R_{CT}$ values measured from a group of healthy people;

detecting the person is in a moderately infected state if the calculated $R_{CT}$ is within a second range of the calibration dataset, the second range of the calibration dataset comprising a second set of $R_{CT}$ values between the threshold value and a severity borderline value, the second set of $R_{CT}$ values measured from a group of patients with moderate levels of cytokines; and detecting the person is in a severely infected state if the calculated $R_{CT}$ is within a third range of the calibration dataset, the third range of the calibration dataset comprising a third set of $R_{CT}$ values more than the severity borderline value, the third set of $R_{CT}$ values measured from a group of patients with high levels of cytokines.

16. The method of claim 12, wherein recording the EIS associated with the blood serum sample comprises:

drawing a blood sample from a person;

separating the blood serum sample from the blood sample by centrifuging the blood sample;

forming a mixture by mixing the blood serum sample with an electrolyte solution comprising at least one metal ion;

putting the mixture in contact with three-integrated electrodes of a biosensor; and recording an EIS from the mixture in contact with the three-integrated electrodes using an electrochemical stimulator-analyzer.

17. The method of claim 16, wherein recording the EIS from the mixture in contact with the three-integrated electrodes comprises recording the EIS of the blood serum sample in contact with the three-integrated electrodes at an AC potential amplitude between 5 mV and 20 mV while sweeping a frequency range between 0.01 Hz and 100 kHz.

18. The method of claim 16, wherein putting the mixture in contact with the three-integrated electrodes of the biosensor comprises dropping the mixture on a surface of three-integrated electrodes of the biosensor, the three-integrated electrodes comprising:

a working electrode comprising a circular-shaped sensing part, the circular-shaped sensing part comprising a bilayer of graphene/copper adhered on a first bilayer of gold/titanium (Au/Ti) deposited on a substrate, the working electrode configured to be an attachment site for the mixture;

a counter electrode comprising a partially annular part placed around the working electrode, the counter electrode comprising a second bilayer of Au/Ti deposited on the substrate, the counter electrode configured to acquire the electrical response from the working electrode; and a reference electrode placed adjacent to both the working electrode and the counter electrode, the reference electrode comprising a third bilayer of Au/Ti deposited on the substrate, the reference electrode configured to adjust a specific voltage between the working and the counter electrodes.

19. The method of claim 18, wherein:

the bilayer of graphene/copper comprises a layer of graphene sheets with a thickness between 0.1 nm and 1 nm deposited on a layer of copper with a thickness between 1 μm and 30 μm, and each of the bilayers of Au/Ti comprises a layer of gold with a thickness between 10 nm and 50 nm deposited on a layer of titanium with a thickness between 3 nm and 10 nm.

* * * * *